(12) United States Patent
Barrett et al.

(10) Patent No.: US 6,770,778 B2
(45) Date of Patent: Aug. 3, 2004

(54) N-(4-SUBSTITUTED PHENYL)-ANTHRANILIC ACID HYDROXAMATE ESTERS

(75) Inventors: Stephen Douglas Barrett, Hartland, MI (US); Michael David Kaufman, Ypsilanti, MI (US); Gordon William Rewcastle, Auckland (NZ); Julie Ann Spicer, Auckland (NZ)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 10/349,826

(22) Filed: Jan. 23, 2003

(65) Prior Publication Data

US 2003/0232889 A1 Dec. 18, 2003

Related U.S. Application Data

(60) Provisional application No. 60/351,106, filed on Jan. 23, 2002.

(51) Int. Cl.$^7$ ................. C07C 239/08; A61K 31/215
(52) U.S. Cl. ............... 560/315; 560/41; 562/450; 564/157; 564/163; 564/164; 564/165; 564/167; 556/419; 514/507; 514/575; 514/534; 514/563; 514/616; 514/770
(58) Field of Search ............... 560/41, 315; 562/450; 564/157, 163, 164, 165, 167; 556/419; 514/507, 575, 534, 563, 616, 770

(56) References Cited

U.S. PATENT DOCUMENTS

| | | | |
|---|---|---|---|
| 2,082,171 A | 6/1937 | Mietzsch et al. | |
| 2,502,451 A | 4/1950 | Goldberg et al. | |
| 2,553,914 A | 5/1951 | Goldberg et al. | |
| 3,781,358 A | 12/1973 | Anderson et al. | |
| 4,510,139 A | 4/1985 | Bailey | |
| 4,921,875 A | 5/1990 | Englert et al. | |
| 5,068,250 A | 11/1991 | Penning et al. | |
| 5,525,625 A | 6/1996 | Bridges | |
| 6,310,060 B1 | 10/2001 | Barrett et al. | |
| 6,696,440 B1 * | 2/2004 | Bridges et al. | 514/231.2 |

FOREIGN PATENT DOCUMENTS

| | | |
|---|---|---|
| EP | 0242559 | 3/1987 |
| EP | 0316630 | 5/1989 |
| GB | 1371378 | 10/1974 |
| WO | WO 93/24442 | 12/1993 |
| WO | WO 97/07790 | 3/1997 |
| WO | WO 97/47270 | 12/1997 |
| WO | WO 98/37881 | 9/1998 |
| WO | WO 99/01421 | 1/1999 |
| WO | WO 99/01426 | 1/1999 |
| WO | WO 99/21840 | 5/1999 |
| WO | WO 00/41505 | 7/2000 |
| WO | WO 02/06213 | 1/2002 |

OTHER PUBLICATIONS

PCT International Search Report PCT/US99/30491.
Hajime Fujimura, "Hydroxamic Acid Derivatives", Chemical Abstracts, Jan. 20, 1969, vol. 70, No. 3, Abstract No. 11330.
F. Hunziker, "Chemistry and Pharmacology of Dibenzo[b,e][1,4]Diazepine Derivatives with Basic Substituents in Position 10", Chemical Abstracts, Oct. 14, 1963, vol. 59, No. 8, Abstract No. 8753f.
V. O. Yu, "Acridine Derivatives as a Source of Antimalarials", Chemical Abstracts, Nov. 20, 1941, vol. 35, No. 22, Abstract No. 7965h.
A. H. Cook, "Pyridlacridines", Chemical Abstracts, Jan. 10, 1944, vol. 38, No. 1, Abstract No. 105.
Hajime Fujimura, et al., "Hydroxamic Acid Derivatives", Database Chemabs Online, Accession No. 1969:11330.
N. A. Mokhort, Dependence Between Structure, Antiinflammatory, Analgesic, and Antipyretic Actions in N–aromatic Deriviatives of Anthranilic Acid, Database Chemabs Online, Accession No. 1972:121461.
Hiroshi Hirano, et al., "Novel N–phenylanthranilic acid derivatives", Database Chemabs Online, Accession No. 1968:418858.
E. S. Endelman, et al., "Synthesis and physiological properties of N–phenylanthranilic acids with fluorine–containing substituents", Database Chemabs Online, Accession No. 1974:70488.
Beilstein Institute Fuer Literature Der Organischen Chemie, Database Crossfire Online, Abstract BRN 3350527.
Fritz Hunziker, et al., Pharmacology of Dibenzo[b,e][1,4] Diazepine Derivatives with Basic Substituents in Position 10, Database Chemabs Online, Accession No. 8753f.
Mikio Takeda, et al., "Synthesis OF Dibenzo[b,e][1,4]Diazepine Derivatives as Anti–Depressants", Database Chemabs Online, Accession No. 1969:403368.
O. U. Magidson, et al., "Acridine Compounds as a Source of Medicinal Products (V)", Database Chemabs Online, Accession No. 35:7965h.
PCT International Search Report PCT/IB03/00210.

* cited by examiner

*Primary Examiner*—Shailendra Kumar
(74) *Attorney, Agent, or Firm*—Peter C. Richardson; Garth Butterfield; Krishna G. Banerjee

(57) ABSTRACT

The present invention relates to oxygenated esters of 4-substituted-phenylamino benzhydroxamic acid derivatives, pharmaceutical compositions, and methods of use thereof.

35 Claims, No Drawings

N-(4-SUBSTITUTED PHENYL)-ANTHRANILIC ACID HYDROXAMATE ESTERS

This application claims the benefit of priority to U.S. provisional application Serial No. 60/351,106 filed Jan. 23, 2002.

FIELD OF THE INVENTION

The present invention relates to oxygenated esters of 4-substituted-phenylamino benzhydroxamic acid derivatives, pharmaceutical compositions, and methods of use thereof.

BACKGROUND OF THE INVENTION

MAPK/ERK Kinase ("MEK") enzymes are dual specificity kinases involved in, for example, immunomodulation, inflammation, and proliferative diseases such as cancer and restenosis.

Proliferative diseases are caused by a defect in the intracellular signaling system, or the signal transduction mechanism of certain proteins. Defects include a change either in the intrinsic activity or in the cellular concentration of one or more signaling proteins in the signaling cascade. The cell may produce a growth factor that binds to its own receptors, resulting in an autocrine loop, which continually stimulates proliferation. Mutations or overexpression of intracellular signaling proteins can lead to spurious mitogenic signals within the cell. Some of the most common mutations occur in genes encoding the protein known as Ras, a G-protein that is activated when bound to GTP, and inactivated when bound to GDP. The above-mentioned growth factor receptors, and many other mitogenic receptors, when activated, lead to Ras being converted from the GDP-bound state to the GTP-bound state. This signal is an absolute prerequisite for proliferation in most cell types. Defects in this signaling system, especially in the deactivation of the Ras-GTP complex, are common in cancers, and lead to the signaling cascade below Ras being chronically activated.

Activated Ras leads in turn to the activation of a cascade of serine/threonine kinases. One of the groups of kinases known to require an active Ras-GTP for its own activation is the Raf family. These in turn activate MEK (e.g., $MEK_1$ and $MEK_2$) which then activates the MAP kinase, ERK ($ERK_1$ and $ERK_2$). Activation of MAP kinase by mitogens appears to be essential for proliferation; constitutive activation of this kinase is sufficient to induce cellular transformation. Blockade of downstream Ras signaling, for example, by use of a dominant negative Raf-1 protein, can completely inhibit mitogenesis, whether induced from cell surface receptors or from oncogenic Ras mutants. Although Ras is not itself a protein kinase, it participates in the activation of Raf and other kinases, most likely through a phosphorylation mechanism. Once activated, Raf and other kinases phosphorylate MEK on two closely adjacent serine residues, $S^{218}$ and $S^{222}$ in the case of MEK-1, which are the prerequisite for activation of MEK as a kinase. MEK in turn phosphorylates MAP kinase on both a tyrosine, $Y^{185}$, and a threonine residue, $T^{183}$, separated by a single amino acid. This double phosphorylation activates MAP kinase at least 100-fold. Activated MAP kinase can then catalyze the phosphorylation of a large number of proteins, including several transcription factors and other kinases. Many of these MAP kinase phosphorylations are mitogenically activating for the target protein, such as a kinase, a transcription factor, or another cellular protein. In addition to Raf-1 and MEKK, other kinases activate MEK, and MEK itself appears to be a signal integrating kinase. Current understanding is that MEK is highly specific for the phosphorylation of MAP kinase. In fact, no substrate for MEK other than the MAP kinase, ERK, has been demonstrated to date and MEK does not phosphorylate peptides based on the MAP kinase phosphorylation sequence, or even phosphorylate denatured MAP kinase. MEK also appears to associate strongly with MAP kinase prior to phosphorylating it, suggesting that phosphorylation of MAP kinase by MEK may require a prior strong interaction between the two proteins. Both this requirement and the unusual specificity of MEK are suggestive that it may have enough difference in its mechanism of action to other protein kinases that selective inhibitors of MEK, possibly operating through allosteric mechanisms rather than through the usual blockade of the ATP binding site, may be found.

It has been found that the compounds of the present invention are inhibitors of MEK and are useful in the treatment of a variety of proliferative disease states, such as conditions related to the hyperactivity of MEK, as well as diseases modulated by the MEK cascade.

SUMMARY OF THE INVENTION

The present invention provides a compound of Formula I

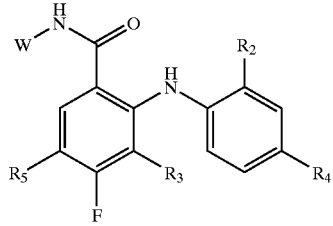

wherein
W is

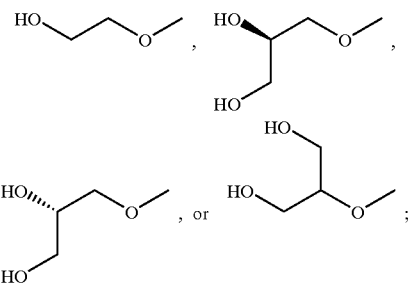

$R_2$ is hydrogen, methyl, fluorine, or chlorine;
$R_3$ is hydrogen or fluorine;
$R_4$ is —$CH_2S(CH_2)_m(CH_3)$, —C≡C—$(CH_2)_q NHCH_3$, —C≡C—$CH_2OCH_3$, (Z)—CHCH$CH_2OCH_3$, —$(CH_2)_n CO_2 R_6$, —$(CF_2)_p CF_3$, —$CH_2(CF_2)_q CF_3$, —$(CH_2)_m CF(CF_3)_2$, —$CH(CF_3)_2$, —$CF_2 CF(CF_3)_2$, —$C(CF_3)_3$, —C≡C—$(CH_2)_q N(CH_3)_2$, —(Z)—CHCH—$(CH_2)_q NHCH_3$, (Z)—CHCH—$(CH_2)_q N(CH_3)_2$, or $C(O)C_{1-3}$ alkyl;
m is 0 to 1;
n is 0 to 2;
p is 1 to 5;
q is 1 to 2;

$R_5$ is hydrogen, fluorine, bromine, or chlorine;

$R_6$ is hydrogen, methyl or ethyl;

and pharmaceutically acceptable salts, ($C_{1-6}$) amides and ($C_{1-6}$) esters thereof.

The present invention provides compounds of Formula I wherein W is

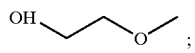

$R_2$ is hydrogen, fluorine, or chlorine; $R_3$ is fluorine; $R_4$ is —$(CH_2)_nCO_2R_6$ where n is 0; $R_4$ is —C≡C—$CH_2OCH_3$; or $R_4$ is $C(O)C_{1-3}$ alkyl; and $R_5$ is hydrogen.

The invention also provides a pharmaceutical composition comprising a compound of Formula I and a pharmaceutically acceptable carrier.

Additionally, the invention provides a method of treating a proliferative disease in a patient in need thereof comprising administering a therapeutically effective amount of a compound of Formula I.

The invention also provides the use of a compound of Formula I for the manufacture of a medicament for the treatment of a proliferative disease.

Furthermore, the invention provides methods of treating cancer, restenosis, psoriasis, autoimmune disease, atherosclerosis, osteoarthritis, rheumatoid arthritis, heart failure, chronic pain, and neuropathic pain in a patient in need thereof comprising administering a therapeutically effective amount of a compound of Formula I.

The invention also provides the use of a compound of Formula I for the manufacture of a medicament for the treatment of cancer, restenosis, psoriasis, autoimmune disease, atherosclerosis, osteoarthritis, rheumatoid arthritis, heart failure, chronic pain, and neuropathic pain.

In addition, the invention provides a method for treating cancer in a patient in need thereof comprising administering a therapeutically effective amount of a compound of Formula I in combination with radiation therapy or at least one chemotherapeutic agent.

DETAILED DESCRIPTION OF THE INVENTION

Certain terms are defined below and by their usage throughout this disclosure.

The terms "halogen" or "halo" in the present invention refer to a fluorine, bromine, chlorine, and iodine atom or fluoro, bromo, chloro, and iodo. The terms fluorine and fluoro, for example, are understood to be equivalent herein.

Alkyl groups, such as "$C_{1-6}$ alkyl", include aliphatic chains (i.e., hydrocarbyl or hydrocarbon radical structures containing hydrogen and carbon atoms) with a free valence. Alkyl groups are understood to include straight chain and branched structures. Examples include methyl, ethyl, propyl, isopropyl, butyl, isobutyl, sec-butyl, t-butyl, pentyl, 2-pentyl, 3-pentyl, isopentyl, neopentyl, (R)-2-methylbutyl, (S)-2-methylbutyl, 3-methylbutyl, 2,3-dimethylpropyl, hexyl, and the like. The term "$C_{1-6}$ alkyl" includes within its definition the terms "$C_{1-4}$ alkyl" and "$C_{1-2}$ alkyl".

Alkenyl groups are analogous to alkyl groups, but have at least one double bond (two adjacent $sp^2$ carbon atoms). Depending on the placement of a double bond and substituents, if any, the geometry of the double bond may be entgegen (E), or zusammen (Z), cis, or trans. Similarly, alkynyl groups have at least one triple bond (two adjacent sp carbon atoms). Unsaturated alkenyl or alkynyl groups may have one or more double or triple bonds, respectively, or a mixture thereof. Like alkyl groups, unsaturated groups may be straight chain or branched. Examples of alkenyls and alkynyls include vinyl, allyl, 2-methyl-2-propenyl, cis-2-butenyl, trans-2-butenyl, and acetyl.

The present invention includes the hydrates and the pharmaceutically acceptable salts and solvates of the compounds defined by Formula I. The compounds of this invention can possess a sufficiently basic functional group, and accordingly react with any of a number of inorganic and organic acids, to form a pharmaceutically acceptable salt.

The term "pharmaceutically acceptable salt" as used herein, refers to salts of the compounds of Formula I which are substantially nontoxic to living organisms. Typical pharmaceutically acceptable salts include those salts prepared by reaction of the compounds of the present invention with a pharmaceutically acceptable mineral or organic acid. Such salts are also known as acid addition salts. Such salts include the pharmaceutically acceptable salts listed in J of Pharm Sci. 1977;66:2–19, which are known to the skilled artisan.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, benzenesulfonic acid, oxalic acid, p-bromophenylsulfonic acid, carbonic acid, succinic acid, citric acid, benzoic acid, acetic acid, and the like. Example of such pharmaceutically acceptable salts are the sulfate, pyrosulfate, bisulfate, sulfite, bisulfite, phosphate, monohydrogenphosphate, dihydrogenphosphate, metaphosphate, pyrophosphate, bromide, hydrobromide, iodide, acetate, propionate, decanoate, caprate, caprylate, acrylate, ascorbate, formate, hydrochloride, dihydrochloride, isobutyrate, caproate, heptanoate, propiolate, glucuronate, glutamate, propionate, phenylpropionate, salicylate, oxalate, malonate, succinate, suberate, sebacate, fumarate, malate, maleate, hydroxymateate, mandelate, mesylate, nicotinate, isonicotinate, cinnamate, hippurate, nitrate, stearate, phthalate, teraphthalate, butyne-1,4-dioate, butyne-1,4-dicarboxylate, hexyne-1,4-dicarboxylate, hexyne-1,6-dioate, benzoate, chlorobenzoate, methylbenzoate, hydrozybenzoate, methoxybenzoate, dinitrobenzoate, o-acetoxybenzoate, naphthalene-2-benzoate, phthalate, p-toluenesulfonate, p-bromobenzenesulfonate, p-chlorobenzenesulfonate, xylenesulfonate, phenylacetate, trifluoroacetate, phenylpropionate, phenylbutyrate, citrate, lactate, α-hydroxybutyrate, glycolate, tartrate, hemitartrate, benzenesulfonate, methanesulfonate, ethanesulfonate, propanesulfonate, hydroxyethanesulfonate, 1-naphthalenesulfonate, 2-naphthalenesulfonate, 1,5-naphthalenedisulfonate, mandelate, tartarate, and the like. A preferred pharmaceutically acceptable salt is hydrochloride.

It should be recognized that the particular counterion forming a part of any salt of this inventions is usually not of a critical nature, so long as the salt as a whole is pharmacologically acceptable and as long as the counterion does not contribute undesired qualities to the salt as a whole. It is further understood that such salts may exist as a hydrate.

As used herein, the term "stereoisomer" refers to a compound made up of the same atoms bonded by the same bonds but having different three-dimensional structures which are not interchangeable. The three-dimensional structures are called configurations. As used herein, the term "enantiomer" refers to each of two stereoisomers whose molecules are nonsuperimposable mirror images of one another. The term "chiral center" refers to a carbon atom to which four different groups are attached. As used herein, the term "diastereomers" refers to stereoisomers which are not enantiomers. The terms "racemate" or "racemic mixture" refer to a mixture of enantiomers.

The enantiomers of compounds of the present invention can be resolved by one of ordinary skill in the art using standard techniques well-known in the art, such as those described by J. Jacques, et al., "Enantiomers, Racemates, and Resolutions", John Wiley and Sons, Inc. 1981. Examples of resolutions include recrystallization techniques or chiral chromatography.

Some of the compounds of the present invention have one or more chiral centers and may exist in a variety of stereoisomeric configurations. As a consequence of these chiral centers, the compounds of the present invention occur as racemates, mixtures of enantiomers and as individual enantiomers, as well as diastereomers and mixtures of diastereomers. All such racemates, enantiomers, and diastereomers are within the scope of the present invention.

The compounds of Formula I can be prepared by techniques and procedures readily available to one of ordinary skill in the art, for example, by following the procedures as set forth in the following Schemes, or analogous variants thereof. These synthetic strategies are further exemplified in Examples below. These Schemes are not intended to limit the scope of the invention in any way.

As used herein, the following terms have the meanings indicated: "BOC" refers to tert-butoxycarbonyl; Celite® refers to a filter agent which is acid washed and approximately 95% $SiO_2$; "DMA" refers to N,N-dimethylacetamide; "DMT-MM" refers to 4-(4,6-dimethoxy-1,3,5-triazin-2-yl)-4-methylmorpholinium chloride; "EtOAc" refers to ethyl acetate; "EtOH" refers to ethanol; "$Et_2O$" refers to diethyl ether; "h" refers to hours; "LiHMDS" refers to lithium 1,1,1,3,3,3-hexamethyldisilazane or lithium bis(trimethylsilylamide);

"Lindlar catalyst" refers to a $Pd/CaCO_3$ catalyst washed with $Pb(OAc)_2$; "Me" refers to methyl; "MeOH" refers to methanol; "MsCl" refers to methane sulfonyl chloride; "Pd/C" refers to palladium on carbon; "$(Ph_3P)_2PdCl_2$" refers to dichlorobis(triphenylphosphine)palladium(II); "$(Ph_3P)_4Pd$" refers to tetrakis(triphenylphosphine)palladium(0); "PyBop" refers to benzotriazole-1-yl-oxy-tris-pyrrolidino-phosphonium hexafluorophosphate; "RT" refers to room temperature; "TEA" refers to triethylamine; "TFA" refers to trifluoroacetic acid; "THF" refers to "tetrahydrofuran; "TLC" refers to thin layer chromatography; and "TMS" refers to trimethylsilyl. All other terms and substituents, unless otherwise indicated, are previously defined. The reagents and starting materials are readily available to one of ordinary skill in the art. Schemes 1 and 2 provide syntheses of the compounds of Formula I.

Scheme 1

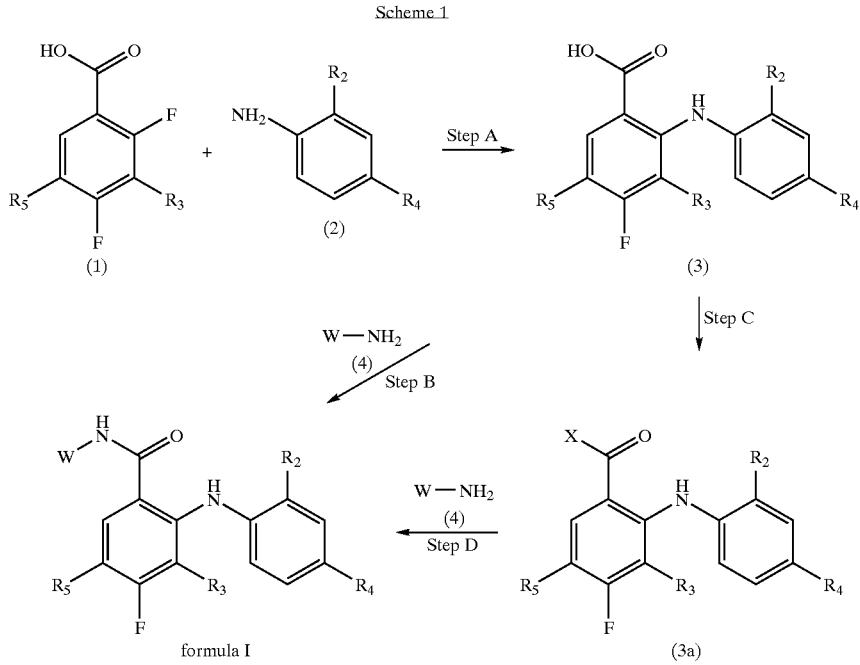

In Scheme 1, Step A, a 2-(arylamino)-benzoic acid or diphenylamine (3) is prepared from the coupling of a suitable benzoic acid (1) and a suitable aniline (2) in the presence of a strong base, for example, lithium 1,1,1,3,3,3-hexamethyldisilazane (LiHMDS), in a polar aprotic solvent such as tetrahydrofuran, acetonitrile or dimethylformamide. For example, the aniline (2) and the benzoic acid (1) are dissolved in a suitable organic solvent and cooled to about −78° C. under nitrogen. The suspension is treated with an excess of a suitable base, such as LiHMDS, and allowed to warm to room temperature. The reaction is typically complete within about 2 hours to about 5 days. The resulting benzoic acid (3) can be isolated by removing the solvent, for example by evaporation under reduced pressure or by filtering the precipitated solid through Celite® and washing with a suitable solvent. The benzoic acid (3) can be further purified, if desired, by standard methods such as chromatography, crystallization, or distillation.

In Scheme 1, Step B, the compounds of Formula I are generally obtained by the union of 2-(arylamino)-benzoic acid (3) with an alkoxylamine (4) by the action of a peptide coupling agent in the presence of a base, if necessary. It is understood that the alkoxylamine (4) may be suitably protected. In such instances, Scheme 1 may be modified to include a removal of the protecting group by a procedure known in the art. Preferred coupling agents include 1,1'-carbonyldiimidazole (CDI), lithium bis (trimethylsilylamide) (LiHMDS), diphenylphosphinic chloride (DPP-Cl), benzotriazol-yl-oxy-tripyrolidinophosphonium hexafluorophosphate (PyBOP), benzotriazol-1-yloxy-tris(dimethylamino)phosphonium hexafluorophosphate (BOP), N,N'-dicyclohexylcarbodiimide (DCC), or 1-ethyl-3-(3-dimethylaminopropyl)carbodiimide hydrochloride (EDCI). Preferred bases include diisopropylethylamine, triethylamine, 4-methylmorpholine, or pyridine or a substituted pyridine, for example, 4-dimethyaminopyridine or 2,6-dimethylpyridine. Preferred solvents are polar aprotic solvents such as dichloromethane, tetrahydrofuran, or dimethylformamide. The reactions are generally carried out at a temperature between about −78° C. to about 25° C., and are normally complete within about 1 hour to about 5 days. The product amide can be isolated by removing the solvent, for example by evaporation under reduced pressure, and further purified, if desired, by standard methods such as chromatography, crystallization, or distillation.

It would be understood by one of skill in the art that the substituent at $R_4$ on the diphenylamine (3) or the substituent at $R_4$ on the compound of Formula I can be reduced before the coupling reaction. The reduction is performed on alkene or alkyne derivatives under conditions known in the art, such as through hydrogenation, for example with Pd/C under an atmosphere of hydrogen.

Alternately, the compounds of formula I are generally prepared as shown in Scheme 1, steps C and D by the contact of alkoxyamine (4) with "activated" benzoic acid derivatives (3a), wherein the activating group "X" completes an acid halide, anhydride, mixed anhydride, or an activated ester, such as a pentafluorophenyl ester, nitrophenyl ester or thioester. Preferred bases include diisopropylethylamine, triethylamine, 4-methylmorpholine, imidazole, pyridine or a substituted pyridine, for example, 4-dimethyaminopyridine or 2,6-dimethylpyridine. Preferred solvents are polar aprotic solvents such as dichloromethane, tetrahydrofuran, or dimethylformamide.

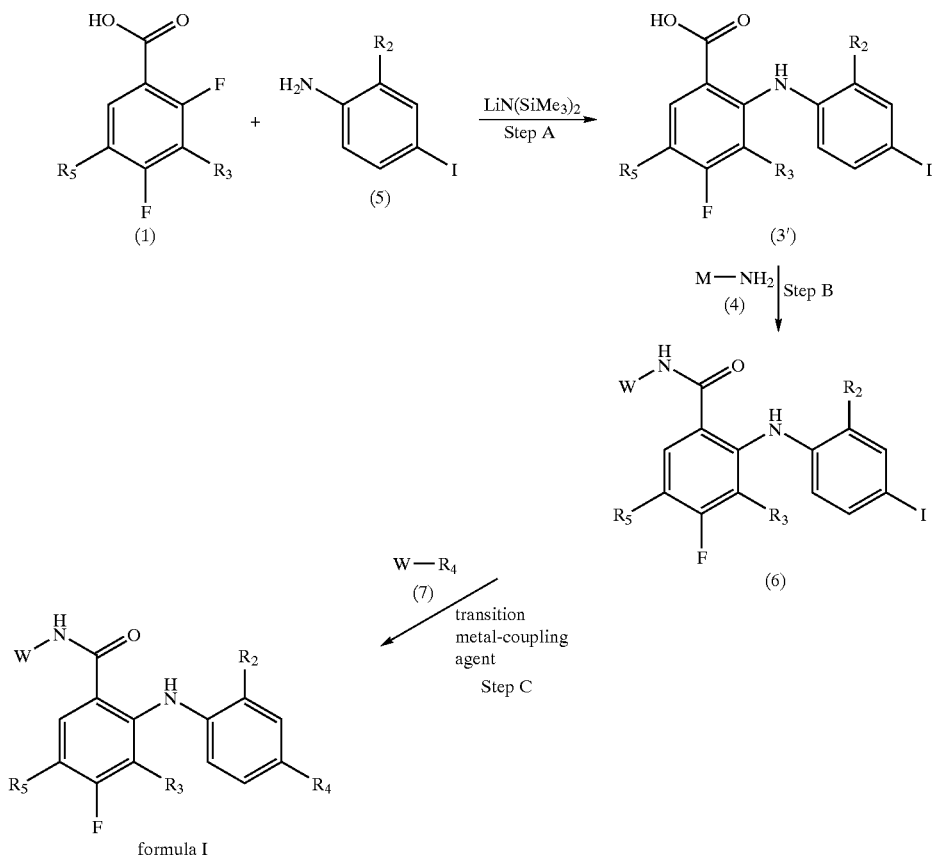

In Scheme 2, Step A, a 4-iodo phenylamino benzoic acid (3') is prepared from the union of a suitable benzoic acid (1) and a suitable 4-iodoaniline (5), according to the general procedure of Scheme 1, Step A.

In Scheme 2, Step B, the 4-iodo phenylamino benzoic acid (3') is coupled with an alkoxylamine (4) according to the general procedure of Scheme 1, Step B or Scheme 1, Steps C and D.

In Scheme 2, Step C, the compounds of Formula I are prepared from the 4-iodo-phenylamino benzamide (6), by transition metal-promoted coupling with reagent M-R$_4$ (7) in a suitable solvent such as triethylamine. The entire mixture is stirred from about 2 to 24 hours at room temperature. The transition metal-promoted coupling may be carried out with a palladium(0) or palladium (II) coupling agent, such as (Ph$_3$P)$_4$Pd or (Ph$_3$P)$_2$PdCl$_2$ and cuprous iodide. M is defined as a functional group known to transfer a carbon radical fragment in transition metal-promoted coupling processes. Examples of a suitable M group include trialkylstannyl, trialkylsilyl, trimethylsilyl, zinc, copper, boron, magnesium and lithium. It would be understood by one of skill in the art that the substituent R$_4$ may be further transformed, such as by oxidation, reduction, deprotection, or hydrogenation. The substituent R$_4$ may also be transformed into a different R$_4$ through standard synthetic procedures known to one of skill in the art. The resulting compound of formula I, as well as the protected Formula I compound, can be isolated by removing the solvent, for example by evaporation under reduced pressure, and further purified, if desired, by standard methods such as chromatography, crystallization, or distillation.

The aniline (2) can be prepared by techniques and procedures readily available to one of ordinary skill in the art and by following the procedures as set forth in the following Schemes, or analogous variants thereof. These Schemes are not intended to limit the scope of the invention in any way.

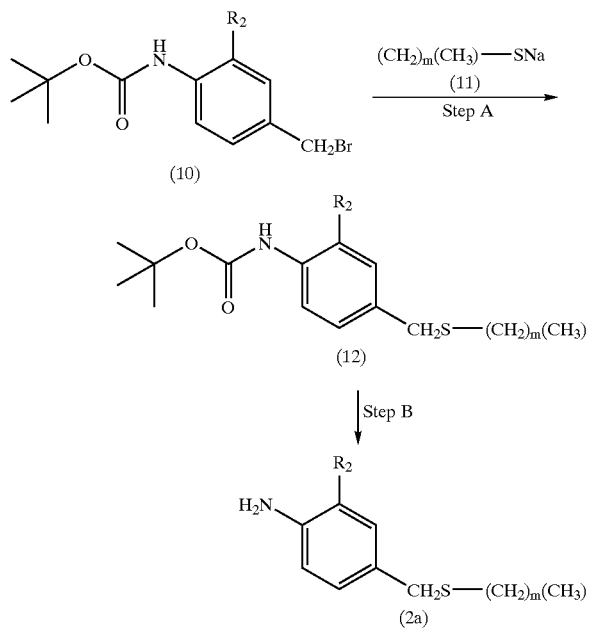

In Scheme 3, Step A, a suitable thiolate (11) is reacted with a 4-tert-butoxycarbonylamino-3-substituted-benzyl bromide, such as 4-tert-butoxycarbonylamino-3-fluorobenzyl bromide (*J Med Chem*. 2000;43:5017) to provide a compound of structure (12). In Step B, the BOC protecting group of compound (12) is hydrolyzed with, for example, TFA to provide the desired aniline (2a).

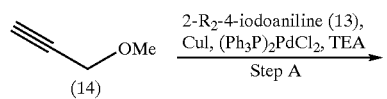

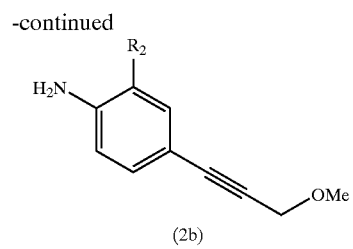

In Scheme 4, Step A, a suitable acetylene (14) such as methylpropargyl ether, and a suitable 4-iodoaniline (13) are coupled via the Sonogashira reaction. For example, a 4-iododaniline (13), such as 2-fluoro-4-iodoaniline, is combined with CuI and (Ph$_3$P)$_2$PdCl$_2$ under nitrogen. An acetylene derivative (14) is added in a suitable solvent, such as TEA, and the entire mixture is stirred for about 2 to 24 hours at room temperature.

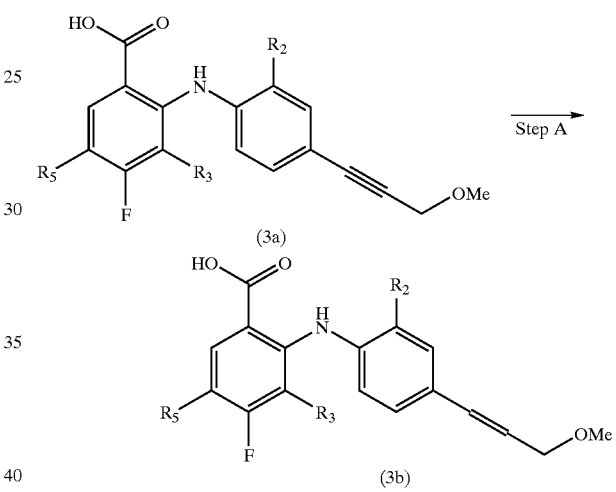

After reaction of the aniline (2b) with a suitable benzoic acid (1) under the standard conditions to form the diphenylamine, as in Scheme 1, Step A above, the alkynyl diphenylamine (3a) is dissolved in a suitable solvent, such as tetrahydrofuran, in the presence of a catalyst, such as Lindlar catalyst or palladium on carbon and, if desired, a suitable compound which disrupts the action of the catalyst, such as quinoline or pyridine. The mixture is stirred under an atmosphere of hydrogen from about 1 to 24 hours at room temperature. The resulting alkenyl diphenylamine (3b) can be isolated by removing the solvent, for example by evaporation under reduced pressure, and further purified, if desired, by standard methods such as chromatography, crystallization, or distillation. Reaction with a suitable alkoxylamine, with the 2-(arylamino)benzoic acids (3a and 3b) under the conditions of Scheme 1, Step B gives the desired compounds of Formula I, wherein R$_4$ is —C≡C—CH$_2$OCH$_3$ or —C=C—CH$_2$OCH$_3$.

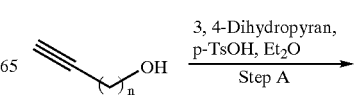

11
-continued
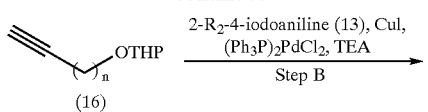
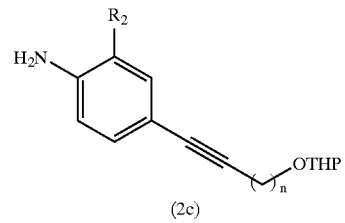
12
-continued
n = 1, 2
THP = tetrahydropyran
In Scheme 6, Step B, a suitable acetylene derivative (16), which has been protected, for example with a tetrahydropyranyl ether, and a suitable 4-iodoaniline (13) such as 2-fluoro-4-iodoaniline are coupled via the Sonogashira reaction as in Scheme 4, Step A, to provide the desired aniline (2c).
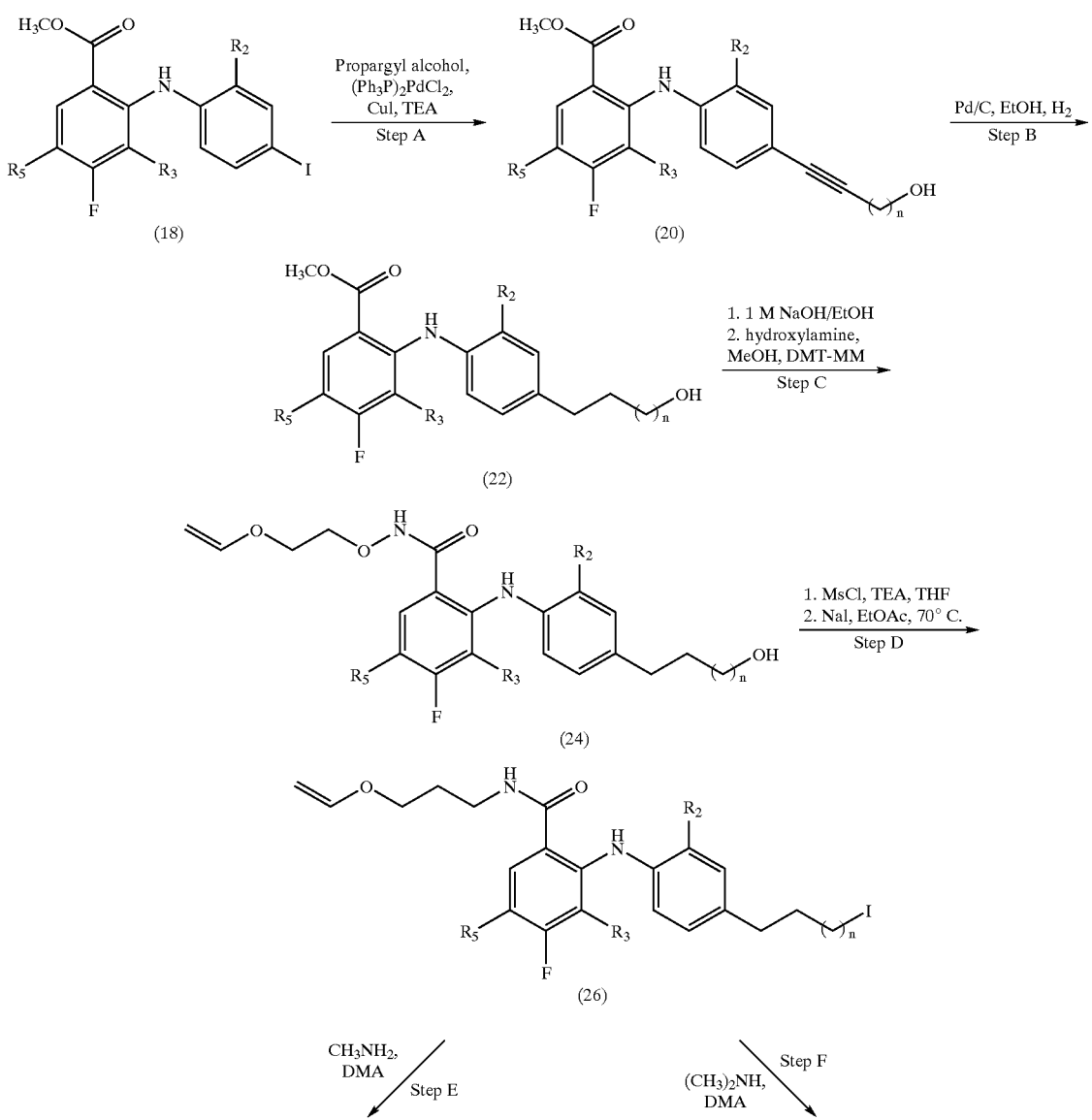

(28)

[Structure showing compound 28 with HO-propyl-NH-C(=O)-benzene ring with R5, R3, F substituents, connected via NH to another benzene ring with R2, and -(CH2)n-NHCH3 side chain]

(30)

[Structure showing compound 30, similar to 28 but with -(CH2)n-N(CH3)2 side chain]

In Scheme 7, Step A, the propargyl alcohol compound (20) is prepared from the iodide compound (18) by transition metal-promoted coupling according to the general procedure of Scheme 2, Step C.

In Scheme 7, Step B, the propargyl alcohol compound (20) is converted to a fully saturated substituent through hydrogenation, for example with Pd/C under an atmosphere of hydrogen to provide the methyl 4-substituted-phenylamino benzoate (22).

In Scheme 7, Step C, methyl 4-substituted-phenylamino benzoate (22) is deprotected in a manner known to one of skill in the art, for example, aqueous NaOH in EtOH, then coupled with an hydroxylamine according to the general procedure of Scheme 1, Step B.

In Scheme 7, step D, the compound (24) is dissolved in a suitable solvent such as tetrahydrofuran and reacted with methanesulfonyl chloride to give the intermediate mesylate, then NaI in EtOAc to give the iodide compound (26).

In scheme 7, steps E and F, the iodide compound (26) is reacted with methylamine and dimethylamine respectively to give compounds of formula I wherein m is 3 and $R_4$ is —(CH2)$_m$NHCH$_3$ (28) and —(CH2)$_m$N(CH$_3$)$_2$ (30).

Scheme 8

[Scheme 8 showing conversion of compound 5 (H2N-benzene-R2 with I) via R4a-I (24) in Step A to compound 2d, then Step B to compound 2e]

$R_{4a}$ is ——(CF$_2$)$_p$CF$_3$, ——(CH$_2$)$_m$CF(CF$_3$)$_2$, ——CF$_2$CF(CF$_3$)$_2$ or

——C(CF$_3$)$_3$, where m is 0

$R_{4b}$ is ——CF$_2$(CF$_2$)$_p$CF$_3$, ——(CH$_2$)$_m$CF(CF$_3$)$_2$, ——CH(CF$_3$)$_2$, or

——C(CF$_3$)$_3$, where m is 1

In Scheme 8, Step A, the desired perfluoroalkyl anilines (2d) are prepared by an Ullmann condensation of a suitable 4-iodoaniline (5), such as 2-fluoro-4-iodoaniline, with a perfluoroalkyl iodide (24), such as CF$_3$(CF$_2$)$_n$I (e.g. N. Yoshino et. al., Bull Chem Soc Jpn, 1992;65:2141).

In Scheme 8, Step B, the desired anilines (2e) are prepared from perfluoroalkyl anilines (2d) by reductive removal of the benzylic fluorine atoms with a suitable reducing agent, such as LiAlH$_4$ (Tetrahedron Letters, 1996;37:4655).

The anilines (5) wherein $R_4$ is —(CH$_2$)$_n$CO$_2$R$_6$, n is 1, and R$_6$ is hydrogen or ethyl are commercially available or can be prepared by one of skill in the art. The anilines (5) wherein $R_4$ is —(CH$_2$)$_n$CO$_2$R$_6$, n is 1, and R$_6$ is methyl are prepared from esterification of the commercially available corresponding aniline with diazomethane. The aniline (5) wherein $R_4$ is —(CH$_2$)$_n$CO$_2$R$_6$, n is 2, and R$_6$ is hydrogen is commercially available or can be prepared by one of skill in the art. The anilines (5) wherein $R_4$ is —(CH$_2$)$_n$CO$_2$R$_6$, n is 2, and R$_6$ is methyl or ethyl are prepared from esterification of the commercially available corresponding aniline with diazomethane.

Scheme 9

[Structure of methyl benzoate with R2 and NH2 substituents]

The anilines of Scheme 9 are used in the preparation of compounds of formula I wherein $R_4$ is —(CH$_2$)$_n$CO$_2$R$_6$, n is 0, and R$_6$ is methyl. The aniline where R2 is hydrogen is commercially available and the aniline where R2 is fluorine can be prepared according to literature procedures available to one of ordinary skill in the art.

Provided by the present invention are compounds of formula I wherein:

W is

[Structure: HO-CH2CH2-O-CH3]

; or

W is

[Structure: HO-CH2-CH(OH)-CH2-O-CH3 (chiral)]

; or

W is

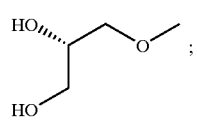

or

W is

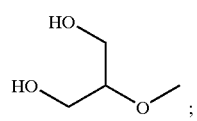

;

$R_2$ is hydrogen, fluorine or chlorine; or $R_2$ is hydrogen or fluorine; or $R_2$ is hydrogen; or $R_2$ is fluorine;

$R_3$ is fluorine;

$R_4$ is —C≡C—CH$_2$OCH$_3$, —(CH$_2$)$_n$CO$_2$R$_6$ or C(O)CH$_3$ alkyl; or $R_4$ is —(CH$_2$)$_n$CO$_2$R$_6$ where n is 0 and $R_6$ is hydrogen or methyl; $R_4$ is CO$_2$H; or $R_4$ is CO$_2$CH$_3$; or $R_4$ is C(O)CH$_3$; or $R_4$ is —C≡C—CH$_2$OCH$_3$; or $R_5$ is hydrogen.

Also provided by the present invention are compounds of Formula

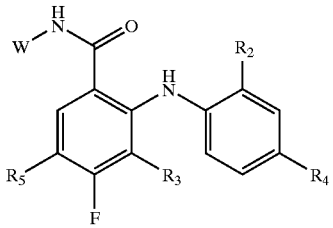

wherein

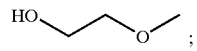

;

W is $R_2$ is hydrogen, fluorine, or chlorine;

$R_3$ is fluorine;

$R_4$ is —CH$_2$S(CH$_2$)$_m$(CH$_3$), —C≡C—CH$_2$OCH$_3$, (Z)—CHCHCH$_2$OCH$_3$, —(CH$_2$)$_n$CO$_2$R$_6$, —(CF$_2$)$_p$CF$_3$, —CH$_2$(CF$_2$)$_q$CF$_3$, —(CH$_2$)$_m$CF(CF$_3$)$_2$, —CH(CF$_3$)$_2$, —CF$_2$CF(CF$_3$)$_2$, —C(CF$_3$)$_3$, —(Z)—CHCH—(CH$_2$)$_q$NHCH$_3$, or (Z)—CHCH—(CH$_2$)$_q$N(CH$_3$)$_2$, or C(O)CH$_3$;

n is 0;

$R_5$ is hydrogen;

$R_6$ is hydrogen or methyl;

and pharmaceutically acceptable salts thereof.

Also provided by the present invention are compounds of Formula

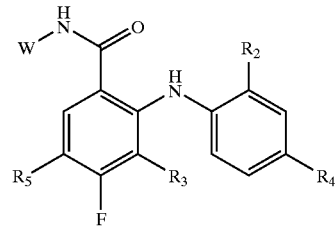

wherein

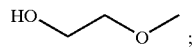

;

W is;

$R_2$ is hydrogen, fluorine, or chlorine;

$R_3$ is fluorine;

$R_4$ is —C≡C—CH$_2$OCH$_3$, —(CH$_2$)$_n$CO$_2$R$_6$ or C(O)CH$_3$;

n is 0;

$R_5$ is hydrogen;

$R_6$ is hydrogen or methyl;

and pharmaceutically acceptable salts thereof.

Particularly, the present invention provides the compounds which are

Methyl 4-[[2,3-difluoro-6-[[(2-hydroxyethoxy)amino]carbonyl]-phenyl]amino]benzoate;

4-[[2,3-Difluoro-6-[[(2-hydroxyethoxy)amino]carbonyl]phenyl]-amino]benzoic acid;

3,4-Difluoro-2-[[2-fluoro-4-(3-methoxy-1-propynyl)phenyl]-amino]-N-(2-hydroxyethoxy)benzamide;

Methyl 4-(2,3-difluoro-6-{[(2-hydroxyethoxy)amino]carbonyl}anilino)-3-fluorobenzoate;

4-(2,3-Difluoro-6-{[(2-hydroxyethoxy)amino]carbonyl}anilino)-3-fluorobenzoic acid;

2-(4-Acetyl-2-chloro-phenylamino)-3,4-difluoro-N-(2-hydroxyethoxy)-benzamide and 2-{2-fluoro-4-[(methylamino)carbonyl]anilino}-3,4-difluoro-N-(2-hydroxyethoxy)benzamide.

Compounds of the present invention include, but are not limited to the following compounds:

Methyl 4-[[2,3-difluoro-6-[[(2-hydroxyethoxy)amino]carbonyl]-phenyl]amino]benzoate;

4-[[2,3-Difluoro-6-[[(2-hydroxyethoxy)amino]carbonyl]phenyl]-amino]benzoic acid; and 3,4-Difluoro-2-[[2-fluoro-4-(3-methoxy-1-propynyl)phenyl]amino]-N-(2-hydroxyethoxy)benzamide.

Also provided by the present invention are compounds which include, but are not limited to the following compounds:

3,4-Difluoro-2-(2-fluoro-4-methylsulfanylmethyl-phenylamino)-N-(2-hydroxy-ethoxy)-benzamide;

2-(4-Ethylsulfanylmethyl-2-fluoro-phenylamino)-3,4-difluoro-N-(2-hydroxy-ethoxy)-benzamide;

3,4-Difluoro-2-[2-fluoro-4-(3-methylamino-prop-1-ynyl)-phenylamino]-N-(2-hydroxy-ethoxy)-benzamide;

3,4-Difluoro-2-[2-fluoro-4-(3-methoxy-prop-1-ynyl)-phenylamino]-N-(2-hydroxy-ethoxy)-benzamide;

3,4-Difluoro-2-[2-fluoro-4-((Z)-3-methoxy-propenyl)-phenylamino]-N-(2-hydroxy-ethoxy)-benzamide;

4-[2,3-Difluoro-6-(2-hydroxy-ethoxycarbamoyl)-phenylamino]-3-fluorobenzoic acid;

4-[2,3-Difluoro-6-(2-hydroxy-ethoxycarbamoyl)-phenylamino]-3-fluorobenzoic acid methyl ester;

4-[2,3-Difluoro-6-(2-hydroxy-ethoxycarbamoyl)-phenylamino]-3-fluorobenzoic acid ethyl ester;

{4-[2,3-Difluoro-6-(2-hydroxy-ethoxycarbamoyl)-phenylamino]-3-fluoro-phenyl}-acetic acid;

{4-[2,3-Difluoro-6-(2-hydroxy-ethoxycarbamoyl)-phenylamino]-3-fluoro-phenyl}-acetic acid methyl ester;

{4-[2,3-Difluoro-6-(2-hydroxy-ethoxycarbamoyl)-phenylamino]-3-fluoro-phenyl}-acetic acid ethyl ester;

3-{4-[2,3-Difluoro-6-(2-hydroxy-ethoxycarbamoyl)-phenylamino]-3-2-fluoro-phenyl}-propionic acid;

3-{4-[2,3-Difluoro-6-(2-hydroxy-ethoxycarbamoyl)-phenylamino]-3-fluoro-phenyl)-propionic acid methyl ester;

3-(4-[2,3-Difluoro-6-(2-hydroxy-ethoxycarbamoyl)-phenylamino]-3-fluoro-phenyl}-propionic acid ethyl ester;

3,4-Difluoro-2-(2-fluoro-4-pentafluoroethyl-phenylamino)-N-(2-hydroxy-ethoxy)-benzamide;

3,4-Difluoro-2-(2-fluoro-4-heptafluoropropyl-phenylamino)-N-(2-hydroxy-ethoxy)-benzamide;

3,4-Difluoro-2-(2-fluoro-4-nonafluorobutyl-phenylamino)-N-(2-hydroxy-ethoxy)-benzamide;

3,4-Difluoro-2-(2-fluoro-4-undecafluoropentyl-phenylamino)-N-(2-hydroxy-ethoxy)-benzamide;

3,4-Difluoro-2-(2-fluoro-4-tridecafluorohexyl-phenylamino)-N-(2-hydroxy-ethoxy)-benzamide;

3,4-Difluoro-2-[2-fluoro-4-(2,2,3,3,3-pentafluoro-propyl)-phenylamino]-N-(2-hydroxy-ethoxy)-benzamide;

3,4-Difluoro-2-[2-fluoro-4-(2,2,3,3,4,4,4-heptafluoro-butyl)-phenylamino]-N-(2-hydroxy-ethoxy)-benzamide;

3,4-Difluoro-2-[2-fluoro-4-(2,3,3,3-tetrafluoro-2-trifluoromethyl-propyl)-phenylamino]-N-(2-hydroxy-ethoxy)-benzamide;

3,4-Difluoro-2-[2-fluoro-4-(1,2,2,2-tetrafluoro-1-trifluoromethyl-ethyl)-phenylamino]-N-(2-hydroxy-ethoxy)-benzamide;

2-(4-Acetyl-2-fluoro-phenylamino)-3,4-difluoro-N-(2-hydroxy-ethoxy)-benzamide;

3,4-Difluoro-2-[2-fluoro-4-(2,2,2-trifluoro-1-trifluoromethyl-ethyl)-phenylamino]-N-(2-hydroxy-ethoxy)-benzamide;

3,4-Difluoro-2-[2-fluoro-4-(1,1,2,3,3,3-hexafluoro-2-trifluoromethyl-propyl)-phenylamino]-N-(2-hydroxy-ethoxy)-benzamide;

3,4-Difluoro-2-[2-fluoro-4-(2,2,2-trifluoro-1,1-bis-trifluoromethyl-ethyl)-phenylamino]-N-(2-hydroxy-ethoxy)-benzamide;

Methyl 4-(2,3-difluoro-6-{[(2-hydroxyethoxy)amino]carbonyl}anilino)-3-fluorobenzoate;

4-(2,3-Difluoro-6-{[(2-hydroxyethoxy)amino]carbonyl}anilino)-3-fluorobenzoic acid;

2-(4-Acetyl-2-chloro-phenylamino)-3,4-difluoro-N-(2-hydroxy-ethoxy)-benzamide and 2-{2-fluoro-4-[(methylamino)carbonyl]anilino}-3,4-difluoro-N-(2-hydroxyethoxy)benzamide.

As used herein, the term "patient" refers to any warm-blooded animal such as, but not limited to, a human, horse, dog, guinea pig, or mouse. Preferably, the patient is human.

The term "treating" for purposes of the present invention refers to treatment, prophylaxis or prevention, amelioration or elimination of a named condition once the condition has been established.

Selective MEK 1 or MEK 2 inhibitors are those compounds which inhibit the MEK 1 or MEK 2 enzymes, respectively, without substantially inhibiting other enzymes such as MKK3, PKC, Cdk2A, phosphorylase kinase, EGF, and PDGF receptor kinases, and C-src. In general, a selective MEK 1 or MEK 2 inhibitor has an $IC_{50}$ for MEK 1 or MEK 2 that is at least one-fiftieth ($\frac{1}{50}$) that of its $IC_{50}$ for one of the above-named other enzymes. Preferably, a selective inhibitor has an $IC_{50}$ that is at least $\frac{1}{100}$, more preferably $\frac{1}{500}$, and even more preferably $\frac{1}{1000}$, $\frac{1}{5000}$, or less than that of its $IC_{50}$ or one or more of the above-named enzymes.

The disclosed compositions are useful as both prophylactic and therapeutic treatments for diseases or conditions related to the hyperactivity of MEK, as well as diseases or conditions modulated by the MEK cascade. Examples include, but are not limited to, stroke, septic shock, heart failure, osteoarthritis, rheumatoid arthritis, organ transplant rejection, and a variety of tumors such as ovarian, lung, pancreatic, brain, prostatic, and colorectal.

The invention further relates to a method for treating proliferative diseases, such as cancer, restenosis, psoriasis, autoimmune disease, and atherosclerosis. Other aspects of the invention include methods for treating MEK-related (including Ras-related) cancers, whether solid or hematopoietic. Examples of cancers include brain, breast, lung, such as non-small cell lung, ovarian, pancreatic, prostate, renal, colorectal, cervical, acute leukemia, and gastric cancer. Further aspects of the invention include methods for treating or reducing the symptoms of xenograft (cell(s), skin, limb, organ or bone marrow transplant) rejection, osteoarthritis, rheumatoid arthritis, cystic fibrosis, complications of diabetes (including diabetic retinopathy and diabetic nephropathy), hepatomegaly, cardiomegaly, stroke (such as acute focal ischemic stroke and global cerebral ischemia), heart failure, septic shock, asthma, Alzheimer's disease, and chronic or neuropathic pain. Compounds of the invention are also useful as antiviral agents for treating viral infections such as HIV, hepatitis (B) virus (HBV), human papilloma virus (HPV), cytomegalovirus (CMV), and Epstein-Barr virus (EBV). These methods include the step of administering to a patient in need of such treatment, or suffering from such a disease or condition, a therapeutically effective amount of a disclosed compound of Formula I or pharmaceutical composition thereof.

The term "chronic pain" for purposes of the present invention includes, but is not limited to, neuropathic pain, idiopathic pain, and pain associated with chronic alcoholism, vitamin deficiency, uremia, or hypothyroidism. Chronic pain is associated with numerous conditions including, but not limited to, inflammation, arthritis, and postoperative pain.

As used herein, the term "neuropathic pain" is associated with numerous conditions which include, but are not limited to, inflammation, postoperative pain, phantom limb pain, burn pain, gout, trigeminal neuralgia, acute herpetic and postherpetic pain, causalgia, diabetic neuropathy, plexus avulsion, neuroma, vasculitis, viral infection, crush injury, constriction injury, tissue injury, limb amputation, arthritis pain, and nerve injury between the peripheral nervous system and the central nervous system.

The invention also features methods of combination therapy, such as a method for treating cancer, wherein the method further includes providing radiation therapy or chemotherapy, for example, with mitotic inhibitors such as a taxane or a vinca alkaloid. Examples of mitotic inhibitors include paclitaxel, docetaxel, vincristine, vinblastine, vinorelbine, and vinflunine. Other therapeutic combinations include a MEK inhibitor of the invention and an anticancer agent such as cisplatin, 5-fluorouracil or 5-fluoro-2-4(1H, 3H)-pyrimidinedione (5FU), flutamide, and gemcitabine.

The chemotherapy or radiation therapy may be administered before, concurrently, or after the administration of a disclosed compound according to the needs of the patient.

Those skilled in the art will be able to determine, according to known methods, the appropriate therapeutically-effective amount or dosage of a compound of the present invention to administer to a patient, taking into account factors such as age, weight, general health, the compound administered, the route of administration, the type of pain or condition requiring treatment, and the presence of other medications. In general, an effective amount or a therapeutically-effective amount will be between about 0.1 and about 1000 mg/kg per day, preferably between about 1 and about 300 mg/kg body weight, and daily dosages will be between about 10 and about 5000 mg for an adult subject of normal weight. Commercially available capsules or other formulations (such as liquids and film-coated tablets) of 100, 200, 300, or 400 mg can be administered according to the disclosed methods.

The compounds of the present invention are preferably formulated prior to administration. Therefore, another aspect of the present invention is a pharmaceutical composition comprising a compound of Formula I and a pharmaceutically acceptable carrier. In making the compositions of the present invention, the active ingredient, such as a compound of Formula I, will usually be mixed with a carrier, or diluted by a carrier or enclosed within a carrier. Dosage unit forms or pharmaceutical compositions include tablets, capsules, pills, powders, granules, aqueous and nonaqueous oral solutions and suspensions, and parenteral solutions packaged in containers adapted for subdivision into individual doses.

Dosage unit forms can be adapted for various methods of administration, including controlled release formulations, such as subcutaneous implants. Administration methods include oral, rectal, parenteral (intravenous, intramuscular, and subcutaneous), intracisternal, intravaginal, intraperitoneal, intravesical, local (drops, powders, ointments, gels, or cream), and by inhalation (a buccal or nasal spray).

Parenteral formulations include pharmaceutically acceptable aqueous or nonaqueous solutions, dispersion, suspensions, emulsions, and sterile powders for the preparation thereof. Examples of carriers include water, ethanol, polyols (propylene glycol, polyethylene glycol), vegetable oils, and injectable organic esters such as ethyl oleate. Fluidity can be maintained by the use of a coating such as lecithin, a surfactant, or maintaining appropriate particle size. Carriers for solid dosage forms include (a) fillers or extenders, (b) binders, (c) humectants, (d) disintegrating agents, (e) solution retarders, (f) absorption acccelerators, (g) adsorbants, (h) lubricants, (i) buffering agents, and (j) propellants.

Compositions may also contain adjuvants such as preserving, wetting, emulsifying, and dispensing agents; antimicrobial agents such as parabens, chlorobutanol, phenol, and sorbic acid; isotonic agents such as a sugar or sodium chloride; absorption-prolonging agents such as aluminum monostearate and gelatin; and absorption-enhancing agents.

The following examples represent typical syntheses of the compounds of the present invention as described generally above. These examples are illustrative only and are not intended to limit the invention in any way. The reagents and starting materials are readily available to one of ordinary skill in the art.

PREPARATION 1

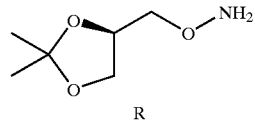

(R)-(2,2-Dimethyl-[1,3]dioxolan-4-ylmethyl)-hydroxylamine

Step A: Preparation of 1,2:5,6-di-O-isopropylidene-D-mannitol

To a stirring suspension of D-Mannitol (1.82 g, 10.0 mmol) in tetrahydrofuran (21 mL) and dimethylformamide (9 mL) was added p-toluenesulfonic acid monohydrate (0.02 g, 0.1 mmol,) at ambient temperature, followed by 2,2-dimethoxypropane (2.8 mL, 0.023 mol). The reaction mixture was stirred for 18 hours at room temperature, then additional 2,2-dimethoxypropane (0.3 mL, 2.4 mmol) was added. The suspension was heated to 40° C. to 45° C., and stirred for 2 hours. Sodium bicarbonate (1.8 g, 0.016 mol) was added to neutralize the acid and the mixture was stirred for 30 minutes. The excess $Na_2CO_3$ was filtered and washed with tetrahydrofuran (5 mL). The filtrate was concentrated. To the remaining light yellow oil was added toluene (15 mL) and the mixture was stirred at 3° C. to 5° C. until a light-yellow gelatinous solid formed. The solid was filtered and washed with hexane (2×5 mL). The product was dried in a vacuum oven for 18 hours to give 1,2:5,6-di-O-isopropylidene-D-mannitol (1.24 g, 47.3%) as an off-white solid, mp 110–113° C.

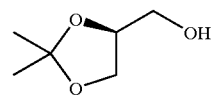

Step B: Preparation of (S)-(+)-(2,2-dimethyl-[1,3]dioxolan-4-yl)-methanol

To a solution of the product of Preparation 1, Step A, 1,2:5,6-di-O-isopropylidene-D-mannitol (50 g, 0.191 mol), in water (700 mL), was added solid sodium bicarbonate (20 g). The resultant solution was stirred until all the solid dissolved, and then cooled in an ice-water bath. Solid sodium periodate (81.5 g, 0.381 mol) was slowly added to the solution portionwise. Gas evolution observed. The white mixture was stirred at ambient temperature for 2 hours. Solid sodium chloride (30 g) was added, and the mixture was stirred for 15 minutes. The white solid was filtered. The filtrate was cooled in an ice-water bath. Solid sodium borohydride was added slowly. Gas bubble evolved. The mixture was warmed to ambient temperature, and stirred overnight. The milky mixture turned to a clear solution. The aqueous solution was extracted with dichloromethane (3×). The organic solution was washed with brine, and dried over magnesium sulfate. The solvent was removed in vacuo to give (S)-(+)-(2,2-dimethyl-[1,3]dioxolan-4-yl)-methanol as a colorless oil, which was dried under high vacuum at ambient temperature overnight, 34.82 g (60%); MS (APCI+)=133 ($M^+$+1).

Step C: Preparation of (R)-2-(2,2-dimethyl-[1,3]dioxolan-4-ylmethoxy)-isoindole-1,3-dione A 3-L round-bottomed flask equipped with mechanical stirrer and additional funnel was charged with N-hydroxyphthalimide (68.0 g, 0.416 mol) and tetrahydrofuran (1.2 L) under nitrogen atmosphere. To this solution was added triphenylphosphine (109.2 g, 0.416 mol) and the product of Preparation 1, Step B, (S)-(2,2-dimethyl-[1,3]dioxolan-4-yl)-methanol (55.0 g, 0.416 mol). The mixture was cooled to 3° C. to 5° C. and diethyl azodicarboxylate (85.2 mL, 0.541 mol) was added dropwise, while keeping the inner temperature below 15° C. The reaction mixture was warmed to ambient temperature, and stirred for 18 hours. The tetrahydrofuran was evaporated under reduced pressure. To the remaining orange solid was added dichloromethane (0.5 L) and the mixture was stirred for 1 hour. The white solid ($Ph_3PO$) was filtered and washed with dichloromethane (0.1 L). The solvent was removed and ethanol (0.5 L) was added to the resulting solid. The mixture was stirred for 2 hours at 3° C. to 5° C. The white solid was filtered, washed with a small amount of cold ETOH, and dried in vacuum oven at 40° C. to give (R)-2-(2,2-dimethyl-[1,3]dioxolan-4-ylmethoxy)-isoindole-1,3-dione (112.5 g, 97%) as a white solid: $^1H$ NMR ($CDCl_3$): δ 1.33 (s, 3H), 1.99 (s, 3H), 3.96 (m, 1H), 4.15 (m, 2H), 4.30 (m, 1H), 4.48 (m, 1H), 7.59 (m, 2H), 7.84 (m, 2H); MS (APCI+)=278 ($M^++1$).

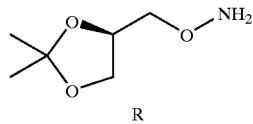

R

Step D: Preparation of (R)-(2,2-dimethyl-[1,3]dioxolan-4-ylmethyl)-hydroxylamine To a stirring solution of the product of Preparation 1, Step C, (R)-2-(2,2-dimethyl-[1,3]dioxolan-4-ylmethoxy)-isoindole-1,3-dione (74.9 g, 0.27 mol) in dichloromethane (480 mL) at 3° C. to 5° C. was added methylhydrazine (15.8 mL, 0.29 mol) dropwise. The color of the suspension turned from yellow to white. The cooling bath was removed and the mixture was stirred for 2 hours at ambient temperature. The resulting suspension was concentrated on a rotary evaporator. To the white solid was added ether (0.5 L) and the resulting mixture was stirred for 1.5 hours at ambient temperature. The white precipitate was filtered and washed with ether (0.2 L). The filtrate was concentrated on rotary evaporator to give (R)-(2,2-dimethyl-[1,3]dioxolan-4-ylmethyl)-hydroxylamine (39.0 g, 98.3%): $^1H$ NMR ($CDCl_3$): δ 1.35 (s, 3H), 1.42 (s, 3H), 3.73 (m, 3H), 4.05 (m, 1H), 4.33 (m, 1H), 5.39 (m, 2H); MS (APCI+)=148.1 ($M^++1$).

PREPARATION 2

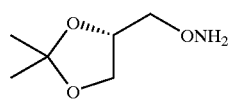

(S)-(2,2-dimethyl-[1,3]dioxolan-4-ylmethyl)-hydroxylamine

Step A: Preparation of L-gulonic γ-lactone

To a solution of L-ascorbic acid (83.9 g, 0.477 mol) in water (600 mL) was added Pd/C (10%, 8.3 g). The mixture was subjected to hydrogenation in a Parr hydrogenator at 48 psi, 18° C. for 62 hours. The reaction mixture was filtered and the filtrate was concentrated in vacuo to afford L-gulonic γ-lactone (81.0 g, 96%) as an off-white solid, after drying at 50° C. in a vacuum oven for 18 hours: mp 182–184° C.

Step B: Preparation of 5,6-isopropylidene-L-gulonic Acid γ-lactone

The product of Preparation 2, Step A, L-gulonic γ-lactone (25.0 g, 140.3 mmol) was dissolved in mixture of tetrahydrofuran (140 mL) and dimethylformamide (200 mL). p-Toluenesulfonic acid monohydrate (2.67 g, 14.0 mmol) was added and the reaction mixture was cooled to 0° C. to 5° C. in an ice-water bath. 2,2-Dimethoxypropane (22.4 mL, 182.4 mmol) was added dropwise and the reaction mixture was stirred at ambient temperature for 18 hours. The mixture was neutralized with solid sodium carbonate (24.0 g) and stirred for 1 hour. The solid was filtered and washed with tetrahydrofuran. The THF was removed under vacuo, and DMF by distillation under high vacuum. The resulting orange solid was triturated with toluene (300 mL), filtered, washed with toluene (20 mL), and dried in a vacuum oven at 40° C. for 3 days, to yield 5,6-isopropylidene-L-gulonic acid γ-lactone (28.9 g, 94%) as a pale orange solid: mp 155–158° C.; MS (APCI+)=219.0 ($M^++1$).

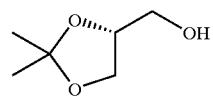

Step C: Preparation of (R)-(+)-(2,2-dimethyl-[1,3]dioxolan-4-yl)-methanol

To a stirring suspension of the product of Preparation 2, Step B, 5,6-O-isopropylidene-L-gulono-1,4-lactone (15.16 g, 69.5 mmol) in water (0.3 L) was added solid sodium periodate in small portions at 3° C. to 5° C. The pH of the mixture was adjusted to 5.5 with 1N aqueous sodium hydroxide. The suspension was stirred for 2 hours at ambient temperature, then saturated with sodium chloride (20.0 g) and filtered. To the filtrate, at 3° C. to 5° C., was added sodium borohydride (10.5 g, 0.278 mol) in small portions. The reaction mixture was stirred for 18 hours at ambient temperature. Acetone (100 mL) was added to destroy the excess of sodium borohydride, and the stirring was continued for 30 minutes. The acetone was removed under reduced pressure, and the aqueous residue was extracted with dichloromethane (3×300 mL) and EtOAc (3×300 mL). The combined organic layers were dried over magnesium sulfate, filtered, and evaporated to give (R)-(+)-(2,2-dimethyl-[1,3]dioxolan-4-yl)-methanol (5.07 g, 55.7%) as a colorless clear liquid: MS (APCI+)=132.9 ($M^++1$).

Step D: Preparation of (S)-2-(2,2-Dimethyl-[1,3]dioxolan-4-ylmethoxy)-isoindole-1,3-dione A 3-L round-bottomed flask equipped with mechanical stirrer and additional funnel was charged with N-hydroxyphthalimide (68.0 g, 0.416 mol) and tetrahydrofuran (1.2 L) under nitrogen atmosphere. To this solution was added triphenylphosphine (109.2 g, 0.416 mol) and (R)-(2,2-dimethyl-[1,3]dioxolan-4-yl)-methanol (55.0 g, 0.416 mol). The mixture was cooled to 3° C. to 5° C. and diethyl azodicarboxylate (85.2 mL, 0.541 mol) was added dropwise, while keeping the inner temperature below 15° C. The reaction mixture was warmed to ambient temperature, and stirred for 18 hours. The tetrahydrofuran was evaporated under reduced pressure. To the remaining orange solid was added dichloromethane (0.5 L) and the mixture was stirred for 1 hour. The white solid ($Ph_3PO$) was filtered and washed with dichloromethane (0.1 L). The solvent was removed and ethanol (0.5 L) was added to the resulting solid. The mixture was stirred for 2 hours at 3° C. to 5° C. The white solid was filtered, washed with a small amount of cold EtOH and dried in vacuum oven at 40° C. to give (S)-2-(2,2-dimethyl-[1,3]dioxolan-4-ylmethoxy)-isoindole-1,3-dione (112.5 g, 97%) as a white solid: $^1H$ NMR ($CDCl_3$): δ 1.33 (s, 3H), 1.99 (s, 3H), 3.96 (m, 1H), 4.15 (m, 2H), 4.30 (m, 1H), 4.48 (m, 1H), 7.59 (m, 2H), 7.84 (m, 2H); MS (APCI+)=278 (M++1).

Step E: Preparation of (S)-(2,2-dimethyl-[1,3]dioxolan-4-ylmethyl)-hydroxylamine To a stirring solution of (S)-2-(2,2-dimethyl-[1,3]dioxolan-4-ylmethoxy)-isoindole-1,3-dione (74.9 g, 0.27 mol) in dichloromethane (480 mL) at 3° C. to 5° C. was added methylhydrazine (15.8 mL, 0.29 mol) dropwise. The color of the suspension turned from yellow to white. The cooling bath was removed and the mixture was stirred for 2 hours at ambient temperature. The resulting suspension was concentrated on a rotary evaporator. To the white solid was added ether (0.5 L) and the resulting mixture was stirred for 1.5 hours at ambient temperature. The white precipitate was filtered and washed with ether (0.2 L). The filtrate was concentrated on rotary evaporator to give (S)-(2,2-dimethyl-[1,3]dioxolan-4-ylmethyl)-hydroxylamine (39.0 g, 98.3%): $^1$H NMR (CDCl$_3$): δ 1.35 (s, 3H), 1.42 (s, 3H), 3.73 (m, 3H), 4.05 (m, 1H), 4.33 (m, 1H), 5.39 (m, 2H); MS (APCI+)= 148.1 (M++1).

PREPARATION 3

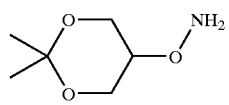

O-(2,2-Dimethyl-[1,3]dioxan-5-yl)-hydroxylamine

Step A: Preparation of 2-(2,2-dimethyl-[1,3]dioxan-5-yloxy)-isoindole-1,3-dione 2,2-Dimethyl-[1,3]dioxan-5-ol was Prepared as Described Previously (Forbes, D. C. et. al. *Synthesis*, 1998;6:879–82). $^1$H NMR (400 MHz; DMSO-d$_6$) δ 4.91 (d, 1H, J=5.1), 3.70–3.75 (m, 2H), 3.41–3.46 (m, 3H), 1.30 (s, 3H), 1.24 (s, 3H); MS (APCI+)=132.9. To a stirring solution of 2,2-dimethyl-[1,3]dioxan-5-ol (1.50 g, 11.35 mmol), N-hydroxyphthalimide (1.85 g, 11.35 mmol) and triphenylphosphine (2.98 g, 11.35 mmol) in anhydrous tetrahydrofuran (30 mL) at 0° C. was added diethyl azodicarboxylate (2.3 mL, 14.75 mmol). The resultant solution was allowed to warm to room temperature. After stirring for 3 hours, the mixture was concentrated in vacuo and charged with chloroform affording white solids. The solids were filtered off and filtrate was collected and concentrated. The residue was purified via silica column chromatography (4:1 hexanes/ethyl acetate) affording 2-(2,2-dimethyl-[1,3]dioxan-5-yloxy)-isoindole-1,3-dione as clear crystals (1.74 g, 55% over 2 steps): $^1$H NMR (400 MHz; DMSO-d$_6$) δ 7.83 (s, 4H), 4.11–4.12 (m, 1H), 4.04–4.09 (m, 2H), 3.92–3.96 (m, 2H), 1.32 (s, 3H), 1.25 (s, 3H); MS (APCI+)=278.0.

Step B: Preparation of O-(2,2-dimethyl-[1,3]dioxan-5-yl)-hydroxylamine

To a stirring solution of the product of Example 13, Step A, 2-(2,2-dimethyl-[1,3]dioxan-5-yloxy)-isoindole-1,3-dione (1.72 g, 6.20 mmol) in dichloromethane (15 mL) at 0° C. under nitrogen was added methylhydrazine (0.36 mL, 6.82 mmol) and allowed to warm to room temperature. After stirring for 2 hours the reaction mixture was concentrated in vacuo and charged with diethylether. The solids were filtered off and the filtrate was collected and concentrated to afford O-(2,2-dimethyl-[1,3]dioxan-5-yl)-hydroxylamine as a yellow oil (0.97 g, 100%). $^1$H NMR (400 MHz; DMSO-d$_6$) δ 5.98 (bs, 2H), 3.84–3.87 (m, 2H), 3.66–3.68 (m, 2H), 3.30–3.35 (m, 1H), 1.29 (s, 3H), 1.22 (s, 3H); MS (APCI+)= 147.9.

EXAMPLE 1

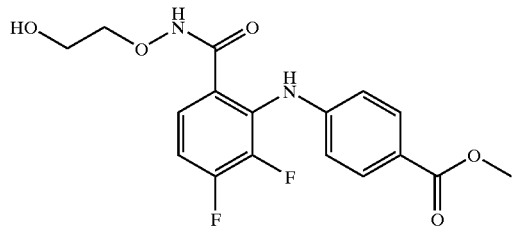

Methyl 4-[[2.3-difluoro-6-[[(2-hydroxyethoxy)amino]carbonyl]phenyl]-amino]benzoate To a solution of 2,3,4-trifluorobenzoic acid (1.00 g, 5.68 mmol) in dry THF (10 mL) at −78° C. under nitrogen was added slowly, lithium bis(trimethylsilyl)amide (5.36 mL, 5.68 mmol, 1.06 M solution in THF). The resulting solution was stirred for 15 minutes at this temperature. This is referred to as Solution A.

To a solution of methyl 4-aminobenzoate (857 mg, 5.68 mmol) in dry THF (10 mL) at −78° C. (outside) under nitrogen was added slowly, lithium bis(trimethylsilyl)amide (10.71 mL, 11.36 mmol, 1.06 M solution in THF). The resulting solution was stirred for 15 minutes. This is referred to as Solution B.

Solution A was transferred to Solution B using positive nitrogen pressure. The reaction mixture was stirred at ambient temperature overnight. The resulting yellow suspension was poured into 1 M HCl solution (150 mL) and extracted with EtOAc (2×100 mL). The EtOAc fractions were then combined and washed with water (200 mL) and brine (200 mL), then dried (Na$_2$SO$_4$), filtered through Celite®, and the solvent removed under reduced pressure to afford crude 3,4-difluoro-2-[[4-(methoxycarbonyl)-phenyl]amino] benzoic acid as a cream solid (1.89 g). $^1$H NMR [400 MHz, (CD$_3$)$_2$SO] δ 13.38 (br s, 1 H), 9.25 (br s, 1 H), 7.84–7.76 (m, 2 H), 7.29–7.13 (m, 2 H), 6.93 (dd, J=8.8, 3.0 Hz, 2 H), 3.84 (s, 3 H).

This material was then coupled directly with 2-(aminooxy)ethanol as follows: The crude 3,4-difluoro-2-[[4-(methoxycarbonyl)-phenyl]amino]benzoic acid was dissolved in dry THF (20 mL) to which was added CDI (1.63 g, 10.0 mmol). This reaction mixture was stirred at room temperature for 2 hours, then a solution of 2-(aminooxy)ethanol (1.55 g, 20.1 mmol) in dry THF (10 mL) was added and the reaction allowed to stir at room temperature overnight. The reaction solvent was removed under reduced pressure and the resulting oil dissolved in EtOAc (200 mL) which was washed sequentially with 1 M HCl (100 mL), water (100 mL), and brine (100 mL). The solution was dried (Na$_2$SO$_4$), the solvent removed under reduced pressure and the crude oil purified by chromatography on flash silica (10% EtOAc as eluant) to give methyl 4-[[2,3-difluoro-6-[[(2-hydroxyethoxy)amino]carbonyl]phenyl]amino] benzoate (0.889 g, 48%) as a white solid; mp (EtOAc/hexanes) 158–160° C. $^1$H NMR [400 MHz, (CD$_3$)$_2$SO] δ 11.64 (br s, 1 H), 8.76 (br s, 1 H), 7.78 (d, J=8.8 Hz, 2 H), 7.41–7.27 (m, 2 H), 6.80 (dd, J=8.8, 1.8 Hz, 2 H), 4.67 (br s, 1 H), 3.78 (s, 3 H), 3.76 (t, J=4.8 Hz, 2 H), 3.50 (t, J=4.6 Hz, 2 H). Anal Calcd for C$_{17}$H$_{16}$F$_2$N$_2$O$_5$: C, 55.7; H, 4.4; N, 7.7. Found C, 55.7; H, 4.4; N, 7.6.

EXAMPLE 2

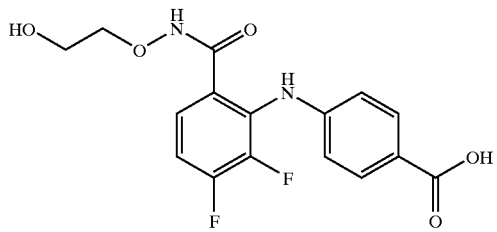

4-[[2,3-Difluoro-6-[[(2-hydroxyethoxy)amino]carbonyl]phenyl]amino]-benzoic acid

The product of Example 1, methyl 4-[[2,3-difluoro-6-[[(2-hydroxyethoxy)amino]carbonyl]phenyl]amino]benzoate (306 mg, 0.84 mmol), was dissolved in ethanol (40 mL), to which was added 1 M NaOH solution (40 mL). This mixture was stirred at room temperature for 15 hours, then poured into 1 M HCl solution (100 mL). The resulting precipitate was extracted with EtOAc (3×80 mL) and the combined EtOAc extracts then combined and washed with water (2×100 mL) and saturated NaCl (100 mL). The organic fraction was dried ($Na_2SO_4$), the solvent removed under reduced pressure, and the resulting residue purified by column chromatography on flash silica (50% EtOAc/hexanes as eluant) to afford 4-[[2,3-difluoro-6-[[(2-hydroxyethoxy)amino]carbonyl]-phenyl]amino]benzoic acid as a crystalline white solid (168 mg, 57%); mp (EtOAc/hexanes) 180–183° C. $^1$H NMR [400 MHz, $(CD_3)_2SO$] δ 11.89 (br s, 2 H), 8.75 (br s, 1 H), 7.75 (d, J=8.8 Hz, 2 H), 7.41–7.25 (m, 2 H), 6.79 (dd, J=8.6, 1.7 Hz, 2 H), 4.76 (br s, 1 H), 3.76 (t, J=4.8 Hz, 2 H), 3.50 (t, J=4.8 Hz, 2 H). Anal. Calcd for $C_{16}H_{14}F_2N_2O_5$: C, 54.5; H, 4.0; N, 8.0. Found C, 54.8; H, 3.9; N, 8.0.

EXAMPLE 3

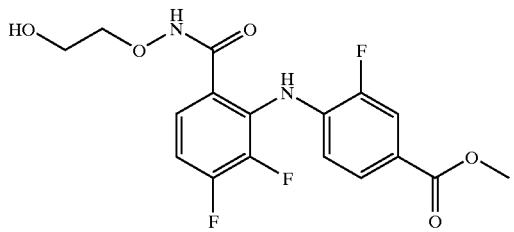

Methyl 4-(2,3-difluoro-6-{[(2-hydroxyethoxy)amino]carbonyl}anilino)-3-fluorobenzoate

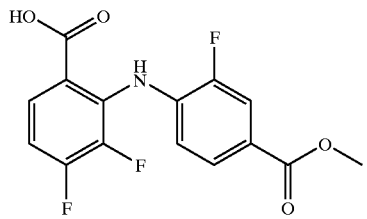

Step A: Preparation of 3,4-difluoro-2-[2-fluoro-4-(methoxycarbonyl)anilino]benzoic acid 2,3,4-Trifluorobenzoic acid and methyl 4-amino-3-fluorocarboxylate [prepared by hydrogenation in the presence of 5% Pd/C of methyl 2-fluoro-4-nitrobenzoate which in turn was prepared according to literature precedent (*J. Org. Chem.,* 1990; 55: 2034–2044)] were reacted in the presence of LiHMDS solution in THF by the general procedure of Example 1. After workup, purification was carried out by chromatography on silica gel (50% EtOAc/PE as eluant) to afford 3,4-difluoro-2-[2-fluoro-4-(methoxycarbonyl)anilino]benzoic acid as a pale yellow solid (26%), which was employed directly in the next step. $^1$H NMR [400 MHz, $(CD_3)_2SO$] δ 13.75 (v br s, 1 H), 10.25 (br s, 1 H), 7.84 (ddd, J=8.4, 5.9, 1.7 Hz, 1 H), 7.74–7.66 (m, 2 H), 7.31–7.23 (m, 1 H), 7.01–6.94 (m, 1 H), 3.83 (s, 3 H). LCMS (APCI–) 324 (M–H).

Step B: Preparation of methyl 4-(2,3-difluoro-6-{[(2-hydroxyethoxy)amino]carbonyl}anilino)-3-fluorobenzoate 3,4-difluoro-2-[2-fluoro-4-(methoxycarbonyl)anilino]benzoic acid (320 mg, 0.99 mmol) was dissolved in MeOH (50 mL) to which was added 2-(aminooxy)ethanol followed by 4-(4,6-dimethoxy-1,3,5-triazin-2-yl)-4-methymorpholinium chloride [DMT-MM, prepared according to the procedure of Kunishima et al [*Tetrahedron,* 55, 13159–13170 (1999)]] (326 mg, 1.18 mmol), This mixture was stirred 15 h. at room temperature. The MeOH was removed under reduced pressure and the resulting oil dissolved in EtOAc (100 mL), which was washed with water (2×100 mL), brine (100 mL) and dried ($Na_2SO_4$). The solvent was removed under reduced pressure to afford a crude yellow oil which was purified by filtration through a plug of silica gel (100% EtOAc as eluant) to give methyl 4-(2,3-difluoro-6-{[(2-hydroxyethoxy)amino]carbonyl}anilino)-3-fluorobenzoate as a cream solid (79%); m.p. (EtOAc/hexane) 162–165° C. $^1$H NMR [400 MHz, $(CD_3)_2SO$] δ 11.82 (v br s, 1 H), 9.08 (v br s, 1 H), 7.70–7.62 (m, 2 H), 7.49–7.43 (m, 1 H), 7.38–7.29 (m, 1 H), 6.81 (ddd, J=8.6, 8.6, 4.7 Hz, 1 H), 4.76 (v br s, 1 H), 3.83–3.78 (m, 5 H), 3.53 (t, J=4.8 Hz, 2 H). Anal. calcd. for $C_{17}H_{15}F_3N_2O_5$: C, 53.1; H, 3.9; N, 7.3. Found C, 53.3; H, 4.2; N, 7.3.

EXAMPLE 4

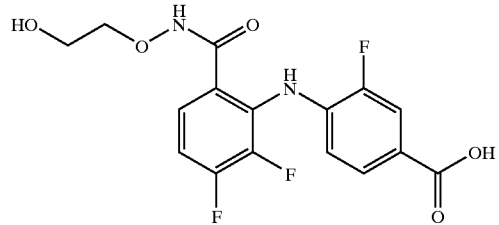

4-(2,3-Difluoro-6-{[(2-hydroxyethoxy)amino]carbonyl}anilino)-3-fluorobenzoic acid Methyl 4-(2,3-difluoro-6-{[(2-hydroxyethoxy)amino]carbonyl}anilino)-3-fluorobenzoate was deprotected using EtOH/1 M NaOH as above to afford, after workup, 4-(2,3-difluoro-6-{[(2-hydroxyethoxy)amino]carbonyl}anilino)-3-fluorobenzoic acid as a cream solid (91%); m.p. (MeOH/EtOAc) 196–200° C. $^1$H NMR [400 MHz, $(CD_3)_2SO$] δ 12.70 (v br s, 1 H), 11.84 (v br s, 1 H), 8.86 (br s, 1 H), 7.67–7.60 (m, 2 H), 7.58–7.41 (m, 1 H), 7.38–7.29 (m, 1 H), 6.81 (ddd, J=8.4, 8.4, 4.5 Hz, 1 H), 4.69 (v br s, 1 H), 3.83 (t, J=4.7 Hz, 2 H), 3.54 (t, J=4.7 Hz, 2H). Anal. calcd. for $C_{16}H_{13}F_3N_2O_5$: C, 51.9; H, 3.5; N, 7.6. Found C, 51.8; H, 3.9; N, 7.3.

EXAMPLE 5

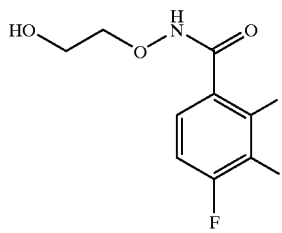

3,4-Difluoro-2-[[2-fluoro-4-(3-methoxy-1-propynyl) phenyl]amino]-N-(2-hydroxyethoxy)benzamide

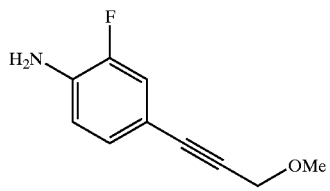

Step A: Preparation of 2-fluoro-4-(3-methoxy-1-propynyl) aniline

2-Fluoro-4-iodoaniline (2.00 g, 8.44 mmol), CuI (32 mg, 0.17 mmol), and $(Ph_3P)_2PdCl_2$ (119 mg, 0.17 mmol) were weighed into a flask which was sealed and flushed with $N_2$. A solution of methyl propargyl ether (0.65 g, 9.28 mmol) in TEA (8 mL) was added, then the entire mixture stirred 15 hours at room temperature. The reaction mixture was diluted with diethyl ether (100 mL), filtered through Celite®, then all solvents removed under reduced pressure. The resulting dark brown oil was purified by filtration through a plug of flash silica (10% EtOAc/hexanes as eluant) to afford 2-fluoro-4-(3-methoxy-1-propynyl)aniline as a pale orange oil which rapidly solidified to give a dark orange solid (1.38 g, 91%); $^1$H NMR [400 MHz, $(CD_3)_2SO$] δ 7.07 (dd, J=12.2, 1.8 Hz, 1 H), 6.98 (dd, J=8.2, 1.7 Hz, 1 H), 6.71 (dd, J=9.3, 8.4 Hz, 1 H), 5.56 (s, 2 H), 4.26 (s, 2 H), 3.29 (s, 3 H).

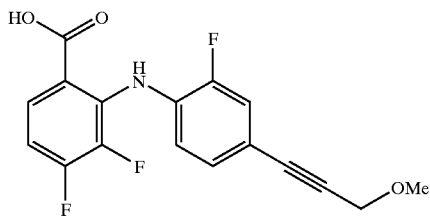

Step B: Preparation of 3,4-difluoro-2-[[2-fluoro-4-(3-methoxy-1-propynyl) phenyl]amino]benzoic acid 2,3,4-Trifluorobenzoic acid and the product of Example 5, Step A, 2-fluoro-4-(3-methoxy-1-propynyl)aniline, were reacted in the presence of LiHMDS solution in THF by the general procedure of Example 1. After workup, followed by purification by chromatography on silica gel (10% EtOAc/hexanes as eluant), 3,4-difluoro-2-[[2-fluoro-4-(3-methoxy-1-propynyl)phenyl]amino]-benzoic acid was isolated (62%) as a pale yellow solid; mp (EtOAc/hexanes) 221–223° C. $^1$H NMR [400 MHz, $(CD_3)_2SO$] δ 13.60 (br s, 1 H), 9.27 (br s, 1 H), 7.85–7.79 (m, 1 H,), 7.36 (dd, J=12.0, 1.8 Hz, 1 H), 7.20 (dd, J=8.3, 1.5 Hz, 1 H), 7.18–7.11 (m, 1 H), 6.96 (td, 8.8, 5.5 Hz, 1 H), 4.31 (s, 2 H), 3.32 (s, 3 H). Anal Calcd for $C_{17}H_{12}F_3NO_3$: C, 60.9; H, 3.6; N, 4.2. Found C, 61.4; H, 3.6; N, 4.2.

Step C: Preparation of 3,4-difluoro-2-[[2-fluoro-4-(3-methoxy-1-propynyl) phenyl]amino]-N-(2-hydroxyethoxy) benzamide The title compound was prepared from reaction of the product of Example 5, Step B, 3,4-difluoro-2-[[2-fluoro-4-(3-methoxy-1-propynyl)phenyl]-amino]benzoic acid. This product (200 mg, 0.60 mmol) was dissolved in dry THF (5 mL) and CDI (193 mg, 1.19 mmol) added. After 0.5 hours at room temperature, TLC showed complete conversion to the desired imidazolide. A solution of 2-(aminooxy)ethanol (184 mg, 2.39 mmol) in dry THF (2 mL) was added and the reaction mixture stirred overnight at room temperature. The reaction solvent was then removed under reduced pressure and the resulting residue partitioned between EtOAc (50 mL) and saturated $NaHCO_3$ solution (50 mL). The EtOAc layer was then dried ($Na_2SO_4$), the solvent removed under reduced pressure, and the resulting oil purified by column chromatography on silica gel (50% EtOAc/hexanes) to give 3,4-difluoro-2-[[2-fluoro-4-(3-methoxy-1-propynyl)phenyl] amino]-N-(2-hydroxyethoxy)benzamide as a white solid (165 mg, 71%); mp (EtOAc/Et$_2$O) 121–123° C. $^1$H NMR [400 MHz, $(CD_3)_2SO$] δ 11.84 (br s, 1 H), 8.85 (br s, 1 H), 7.46–7.38 (m, 1 H), 7.32 (dd, J=12.1, 1.7 Hz, 1 H), 7.29–7.21 (m, 1 H), 7.14 (dd, J=8.4, 1.6 Hz, 1 H), 6.79 (td, J=8.8, 4.7 Hz, 1 H), 4.74 (br s, 1 H), 4.30 (s, 2 H), 3.84 (t, J=4.8 Hz, 2 H), 3.56 (t, J=4.9 Hz, 2 H), 3.32 (s, 3 H). Anal. Calcd for $C_{19}H_{17}F_3N_2O_4$: C, 57.9; H, 4.4; N, 7.1. Found C, 57.9; H, 4.3; N, 7.0.

EXAMPLE 6

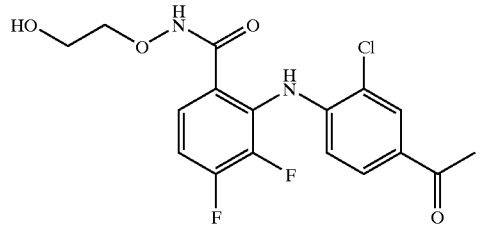

2-(4-Acetyl-2-chloro-phenylamino)-3,4-difluoro-N-(2-hydroxy-ethoxy)-benzamide

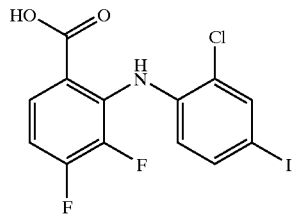

Step A: Preparation of 2-(2-chloro-4-iodophenylamino)-3,4-difluorobenzoic acid

To a solution of 2,3,4-trifluorobenzoic acid (75 g, 0.426 mol) in anhydrous tetrahydrofuran at −78° C. under nitrogen was added slowly lithium bis(trimethylsilyl)amide (426 mL, 0.426 mol, 1.0 M solution in THF). The dark brown reaction mixture was stirred for 15 min at −65° C. (inside temp). This is referred to as Solution A.

To a solution of 2-chloro-4-iodoaniline (108 g, 0.426 mol) in anhydrous tetrahydrofuran (1000 mL) at −78° C. (outside) under nitrogen was added slowly lithium bis(trimethylsilyl) amide (852 ml, 0.852 mol, Aldrich, 1.0 M solution in THF). The dark green solution was stirred for 0.5 h. This is referred to as Solution B.

Solution A was transferred to Solution B using positive nitrogen pressure. The reaction mixture was stirred at ambient temperature overnight. The reaction was quenched with 2.5 L dry ether (saturated with hydrogen chloride gas) until the pH was about 1.0. The precipitated solid was filtered off through Celite® and washed thoroughly with ether.

The filtrate was washed with 1 N HCl (2×500 mL), brine (2×500 mL), dried and concentrated to give a light brown solid (143 g) which was crystallized from methanol (450 mL) and methylene chloride (1.25 L) to afford 2-(2-chloro-4-iodophenylamino)-3,4-difluorobenzoic acid (104 g, 60% yield) as an off-white powder: mp: 226–227° C.; $^1$H NMR (400 MHz, DMSO-d$_6$) δ 13.83 (br s), 9.26 (s), 7.85 (ddd, J=8.9, 6.1, 1.9 Hz, 1 H), 7.81 (d, J=1.9 Hz, 1 H), 7.54 (dd, J=8.6, 1.9 Hz, 1 H), 7.18 (dt, J=7.3, 9.3 Hz, 1 H), 6.74 (dd, J=8.5, 7.1 Hz, 1 H); $^{19}$F-NMR (376 MHz, DMSO-d$_6$) δ −129.9, −141.9. Anal. Calcd/found for $C_{13}H_7NO_2F_2ClI$: C, 38.13/37.33; H, 1.72/1.60; N, 3.42/3.31.

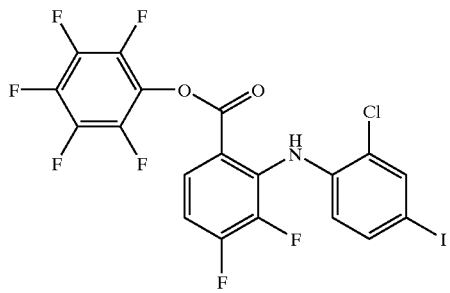

Step B: Preparation of 2-(2-chloro-4-iodophenylamino)-3,4-difluorobenzoic acid pentafluorophenyl ester To a solution of the product of Example 6, Step A, 2-(2-chloro-4-iodophenylamino)-3,4-difluorobenzoic acid (10.0 g, 24.4 mmol), and pyridine (2.16 mL, 26.8 mmol) in anhydrous dimethylformamide (49 mL) was added pentafluorophenyl trifluoroacetate (5.35 mL, 30.5 mmol). The resultant solution was stirred at ambient temperature for 2 h. The reaction mixture was diluted with ethyl acetate (600 mL) and washed with 0.1 M aqueous hydrochloric acid (2×240 mL), 25% saturated aqueous sodium bicarbonate (2×240 mL), and saturated brine (240 mL). The organics were dried over anhydrous magnesium sulfate and concentrated under reduced pressure to afford an oil that was purified on silica gel. Elution with hexanes-ethyl acetate (19:1) afforded 2-(2-chloro-4-iodophenylamino)-3,4-difluorobenzoic acid pentafluorophenyl ester (12.8 g, 91%) as a pale-yellow powder: mp. 108.5–110.0° C.; $^1$H-NMR (400 MHz, CDCl$_3$) δ 8.77 (br s, 1H), 8.07 (br s, 1 H), 7.69 (br s, 1H), 7.48 (br d, J=7.0 Hz, 1H), 6.91 (br d, J=7.2 Hz, 1H), 6.67 (br s., 1H); $^{19}$F-NMR (376 MHz, CDCl$_3$) δ −123.74 (s, 1F), −139.17 (d, J=16.8 Hz, 1F), −152.35 (d, J=21.4 Hz, 2F), −156.96 (t, J=21.4 Hz, 1F), −161.81 (t, J=21.4 Hz, 2F). Anal. Calcd/found for $C_{19}H_6NO_2F_7ClI$: C, 39.65/39.32; H, 1.05/0.91; N, 2.43/2.35; F, 23.10/22.85; Cl, 6.16/6.92; I, 22.05/22.50.

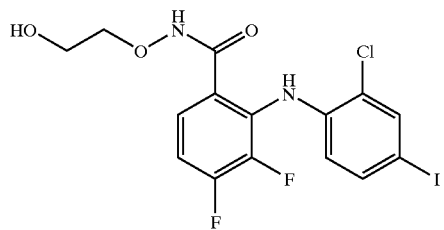

Step C: Preparation of 2-(2-chloro-4-iodo-phenylamino)-3,4-difluoro-N-(2-hydroxy-ethoxy)-benzamide To a solution of the product of Example 6, Step B, 2-(2-chloro-4-iodophenylamino)-3,4-difluorobenzoic acid pentafluorophenyl ester (10.0 g, 17.4 mmol), in anhydrous dimethylformamide (36 mL) was added 2-(aminooxy)-ethanol [prepared by the literature procedure: Dhanak, D.; Reese, C. B. J. Chem. Soc., Perkin Trans. 1 1987, 2829] (1.6 g, 20.8 mmol) and N,N-diisopropylethylamine (6.0 mL, 34.8 mmol). The resultant solution was stirred at ambient temperature for 16 h. The reaction mixture was concentrated to 20% volume then diluted with ethyl acetate (360 mL). The resultant solution was washed with water (6×60 mL) and brine (2×60 mL). The organics were dried over anhydrous magnesium sulfate and concentrated under reduced pressure to afford a white solid that was purified on silica gel. Elution with ethyl acetate-methanol (9:1) afforded 2-(2-chloro-4-iodo-phenylamino)-3,4-difluoro-N-(2-hydroxy-ethoxy)-benzamide (7.31 g, 90%) as a white solid. Recrystallization from methanol afforded analytically pure material: m.p. 173–175° C.; $^1$H NMR (400 MHz, DMSO-d$_6$) δ 11.93 (br s, 1 H), 8.85 (br s, 1 H), 7.76 (d, J=1.7 Hz, 1 H), 7.48 (dd, J=8.6, 1.7 Hz, 1 H), 7.44 (dd, J=8.5, 6.2 Hz, 1 H), 7.25 (dt, J=8.5, 9.3 Hz, 1 H), 6.58 (dd, J=8.5, 6.4 Hz, 1 H), 4.70 (br s, 1 H), 3.86 (br s, 2 H), 3.56 (br d, J=3.9 Hz, 2 H); MS (APCI+)=469.0; MS (APCI−)=467.0; Anal. Calcd/found for $C_{15}H_{12}ClF_2lN_2O_3$: C, 38.45/38.60; H, 2.58/2.53; N, 5.98/5.91; F, 8.11/8.08; I, 27.08/27.43.

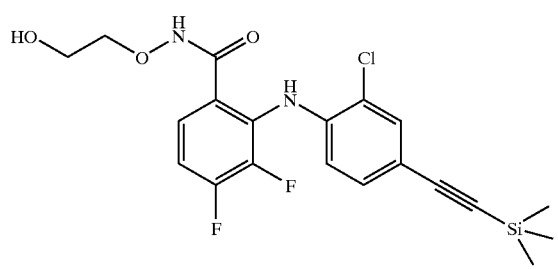

Step D: Preparation of 2-(2-chloro-4-trimethylsilanylethynyl-phenylamino)-3,4-difluoro-N-(2-hydroxy-ethoxy)-benzamide The product of Example 6, Step C, 2-(2-chloro-4-iodo-phenylamino)-3,4-difluoro-N-(2-hydroxy-ethoxy)-benzamide (3.25 g, 6.93 mmol) and (trimethylsilyl)acetylene (1.10 mL, 7.78 mmol) were combined in triethylamine (17 mL). Dichlorobis(triphenylphosphine)-palladium(II) (0.120 g, 0.017 mol) and cuprous iodide (0.033 g, 0.17 mmol) were added and the resultant solution was stirred at ambient temperature for 22 h. The reaction mixture was adsorbed onto Celite® for 20 min and was filtered, washing with ethyl acetate. The filtrate was concentrated to a thick oil, further diluted with ethyl acetate (100 mL) and washed with aqueous citric acid (2 M, 2×25 mL), water, and brine. The organic layer was then dried over magnesium sulfate and concentrated in vacuo to afford a tan-colored solid. Recrystallization form heptane-ethyl acetate afforded 2-(2-chloro-4-trimethylsilanylethynyl-phenylamino)-3,4-difluoro-N-(2-hydroxy-ethoxy)-benzamide (2.34 g, 76% yield) as a grey-colored solid: $^1$H NMR (400 MHz, DMSO-d$_6$) δ 11.96 (s, 1 H), 8.95 (s, 1 H), 7.53 (d, J=1.7 Hz, 1 H), 7.47 (m, 1 H), 7.32 (m, 1 H), 7.27 (dd, J=8.4, 1.8 Hz, 1 H), 6.72 (dd, J=8.0, 6.6 Hz, 1 H), 4.73 (t, J=5.5 Hz, 1 H), 3.87 (apparent t, J=4.7 Hz, 2 H), 3.57 (m, 2 H), 0.21 (s, 9 H); MS (APCI+)=439.1; MS (APCI−)=437.1.

Step E: Preparation of 2-(4-acetyl-2-chloro-phenylamino)-3,4-difluoro-N-(2-hydroxy-ethoxy)-benzamide A solution of 2-(2-chloro-4-trimethylsilanylethynyl-phenylamino)-3,4-difluoro-N-(2-hydroxy-ethoxy)-benzamide (452 mg, 1.03 mmol) in dichloromethane (25 mL) was treated with polystyrene-bound p-toluenesulfonic acid (Argonaut, 1.5 mmol/g, 1.05 g). The resultant mixture was agitated at ambient temperature. After 3.5 h, the reaction mixture was filtered and the resin beads were washed with a solution comprised of dichloromethane-methanol-30% aqueous ammonium hydroxide (100:10:1, 60 mL). The filtrate and washings were concentrated in vacuo and partitioned between ethyl acetate (100 mL) and water (20 mL). The organic layer was washed with water and brine, dried over magnesium sulfate and concentrated in vacuo to afford a straw-colored foam. Recrystallization from dichloromethane-methanol afforded 2-(4-Acetyl-2-chloro-phenylamino)-3,4-difluoro-N-(2-hydroxy-ethoxy)-benzamide as a white solid (113 mg): m.p. 161.5–162.5° C.; $^1$H NMR (400 MHz, DMSO-d$_6$) δ 11.93 (s, 1 H), 8.99 (s, 1 H), 7.99 (d, J=1.7 Hz, 1 H), 7.77 (dd, J=8.5, 1.7 Hz, 1 H), 7.49 (m, 1 H), 7.39 (m, 1 H), 6.78 (dd, J=8.3, 6.3 Hz, 1 H), 4.71 (br s, 1 H), 3.86 (br s, 2 H), 3.56 (br s, 2 H), 2.51 (s, 3 H); MS (APCI+)=385.0; MS (APCI−)=383.0; Anal. Calcd/found for C$_{17}$H$_{15}$ClF$_2$N$_2$O$_4$+0.06 eq CH$_2$Cl$_2$: C, 52.56/52.52; H, 3.91/3.69; N, 7.19/7.07. Concentration of the mother liquor afforded an additional crop of crystals (147 mg, 66% total yield).

EXAMPLE 7

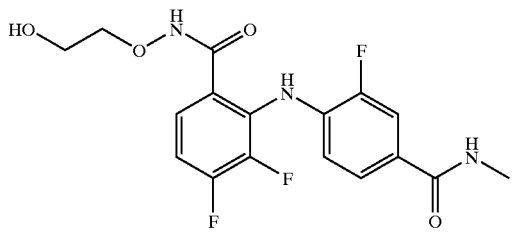

2-{2-fluoro-4-[(methylamino)carbonyl]anilino}-3,4-difluoro-N-(2-hydroxyethoxy)benzamide

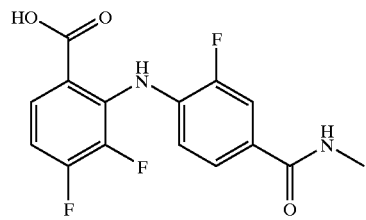

Step A: Preparation of 3,4-difluoro-2-{2-fluoro-4-[(methylamino)carbonyl]anilino}benzoic acid 2,3,4-Trifluorobenzoic acid and 4-amino-3-fluoro-N-methylbenzamide [Anker et al, Helv. Chim. Acta., 67(3), 706–716 (1984)] were reacted in the presence of LiHMDS solution in THF by the general procedure of Example 1, Step B. After workup, followed by purification by chromatography on silica gel (100% EtOAc as eluant), 3,4-difluoro-2-{2-fluoro-4-[(methylamino)carbonyl]anilino}-benzoic acid was isolated as a pale, yellow-orange solid; m.p. (EtOAc/MeOH) 242–244° C. $^1$H NMR [400 MHz, (CD$_3$)$_2$SO] δ 13.70 (v br s, 1 H), 9.28 (br s, 1 H), 8.36 (br d, J=4.5 Hz, 1 H), 7.88–7.80 (m, 1 H) 7.69 (dd, J=12.5, 1.7 Hz, 1 H), 7.60 (dd, J=8.5, 1.5 Hz, 1 H), 7.19 (dd, J=16.7, 9.3 Hz, 1 H), 7.01 (ddd, J=8.6, 8.6, 5.8 Hz, 1 H), 2.77 (d, J=4.4 Hz, 3 H). Anal. calcd. for C$_{15}$H$_{11}$F$_3$N$_2$O$_3$: C, 55.6; H, 3.4; N, 8.6. Await Found.

Step B: Preparation of 2-{2-fluoro-4-[(methylamino)carbonyl]anilino}-3,4-difluoro-N-(2-hydroxyethoxy)benzamide The title compound was prepared from reaction of 3,4-difluoro-2-{2-fluoro-4-[(methylamino)carbonyl]anilino}benzoic acid with 2-(aminooxy)ethanol and DMT-MM by the general procedure of Example 3, Step B, then purified by column chromatography on silica gel (10% MeOH/CH$_2$Cl$_2$ as eluant) to give 2-{2-fluoro-4-[(methylamino)carbonyl]anilino}-3,4-difluoro-N-(2-hydroxyethoxy)benzamide as a crystalline cream solid (45%); m.p. (acetone) 197–200° C. $^1$H NMR [400 MHz, (CD$_3$)$_2$SO] δ 11.84 (br s, 1 H), 8.86 (br s, 1 H), 8.31 (br q, J=4.3 Hz, 1 H), 7.65 (dd, J=12.6, 1.8 Hz, 1 H), 7.55 (dd, J=8.4, 1.8 Hz, 1 H), 7.47–7.41 (m, 1 H), 7.27 (dd, J=16.9, 9.5 Hz, 1 H), 6.84 (ddd, J=8.6, 8.6, 4.8 Hz, 1 H), 4.72 (v br s, 1 H), 3.84 (t, J=4.8 Hz, 2 H), 3.56 (t, J=4.8 Hz, 2 H), 2.76 (d, J=4.5 Hz, 3 H). Anal. calcd. for C$_{17}$H$_{16}$F$_3$N$_3$O$_4$: C, 53.3; H, 4.2; N, 11.0. Await Found.

EXAMPLE 8

Cellular Assay for Measuring MEK Inhibition

The evaluation of the compounds as MEK inhibitors is performed in an assay that measures their ability to inhibit phosphorylation of MAP kinase (ERK) in murine colon 26 (C26) carcinoma cells. Since ERK1 and ERK2 represent the only known substrates for MEK, measurement of inhibition of ERK phosphorylation in cells provides direct readout of cellular MEK inhibition by the compounds of the invention. Briefly, the assay involves treating exponentially growing C26 cells with varying concentrations of the test compound (or vehicle control) for 1 hour at 37° C. Cells are then rinsed free of compound/vehicle and lysed in a solution containing 70 mM NaCl, 50 mM glycerol phosphate, 10 mM HEPES, pH 7.4, 1% Triton X-100, 1 mM Na$_3$VO$_4$, 100 µM PMSF, 10 µM leupeptin, and 10 µM pepstatin. Supernatants are then subjected to gel electrophoresis and Western blotting using a primary antibody recognizing dually phosphorylated ERK1 and ERK2. To evaluate total MAPK levels, blots were subsequently 'stripped' and re-probed with a 1:1 mixture of polyclonal antibodies recognizing unphosphorylated ERK1 and ERK2.

The inhibition data generated by the above protocol is disclosed in Table 1. If several concentrations of inhibitor were tested, IC$_{50}$ values (the concentration which gives 50% inhibition) were determined graphically from the dose response curve for % inhibition. Otherwise, percent inhibitions at measured concentrations are reported.

Table 1. Cellular Inhibition of ERK Phosphorylation by Compounds of the Invention

TABLE I

Cellular Inhibition of ERK Phosphorylation by Compounds of the Invention

| Compound of Example No. | $IC_{50}$ ($\mu$M) |
| --- | --- |
| 1 | >1.000000 |
| 2 | 0.073 |
| 3 | 0.027 |
| 4 | >1.000000 |
| 5 | >1.000000 |
| 7 | >10.00000 |

EXAMPLE 9
Carrageenan-Induced Footpad Edema (CFE) Rat Model

Male outbred Wistar rats (135–150 g, Charles River Labs) are dosed orally with 10 mL/kg vehicle or test compound 1 hour prior to administration of a sonicated suspension of carrageenan (1 mg/0.1 mL saline). Carrageenan is injected into the subplantar region of the right hind paw. Paw volume is determined by mercury plethysmography immediately after injection and again 5 hours after carrageenan injection. Percent inhibition of edema is determined, and the ID40 calculated by linear regression. Differences in swelling compared to control animals are assessed by a 1-way ANOVA, followed by Dunnett's test.

EXAMPLE 10
Collagen-Induced Arthritis in Mice

Type II collagen-induced arthritis (CIA) in mice is an experimental model of arthritis that has a number of pathologic, immunologic, and genetic features in common with rheumatoid arthritis. The disease is induced by immunization of DBA/1 mice with 100 $\mu$g Type II collagen, which is a major component of joint cartilage, delivered intradermally in Freund's complete adjuvant. The disease susceptibility is regulated by the Class II MHC gene locus, which is analogous to the association of rheumatoid arthritis with HLA-DR4.

A progressive and inflammatory arthritis develops in the majority of mice immunized, characterized by paw width increases of up to 100%. A test compound is administered to mice in a range of amounts, such as 20, 60, 100, and 200 mg/kg body weight/day. The duration of the test can be several weeks to a few months, such as 40, 60, or 80 days. A clinical scoring index is used to assess disease progression from erythema and edema (Stage 1), joint distortion (Stage 2), to joint ankylosis (Stage 3). The disease is variable in that it can affect one or all paws in an animal, resulting in a total possible score of 12 for each mouse. Histopathology of an arthritic joint reveals synovitis, pannus formation, and cartilage and bone erosions. All mouse strains that are susceptible to CIA are high antibody responders to Type II collagen, and there is a marked cellular response to CII.

EXAMPLE 11
SCW-Induced Monoarticular Arthritis

Arthritis is induced as described by Schwab, et al., *Infection and Immunity*, 1991;59:4436–42 with minor modifications. Rats receive 6 $\mu$g sonicated SCW (in 10 $\mu$L Dulbecco's PBS [DPBS]) by an intraarticular injection into the right tibiotalar joint on Day 0. On Day 21, the DTH is initiated with 100 $\mu$g of SCW (250 $\mu$L) administered IV. For oral compound studies, compounds are suspended in vehicle (0.5% hydroxypropyl-methylcellulose/0.2% Tween 80), sonicated, and administered twice daily (10 mL/kg volume) beginning 1 hour prior to reactivation with SCW. Compounds are administered in amounts between 10 and 500 mg/kg body weight/day, such as 20, 30, 60, 100, 200, and 300 mg/kg/day. Edema measurements are obtained by determining the baseline volumes of the sensitized hindpaw before reactivation on Day 21, and comparing them with volumes at subsequent time points such as Day 22, 23, 24, and 25. Paw volume is determined by mercury plethysmography.

EXAMPLE 12
Mouse Ear-Heart Transplant Model

Fey, TA et al., describe methods for transplanting split-heart neonatal cardiac grafts into the ear pinna of mice and rats (*J Pharm and Toxic Meth.* 1998;39:9–17). Compounds are dissolved in solutions containing combinations of absolute ethanol, 0.2% hydroxypropyl methylcellulose in water, propylene glycol, cremophor, and dextrose, or other solvent or suspending vehicle. Mice are dosed orally or intraperitoneally once, twice, or three times daily from the day of transplant (Day 0) through Day 13 or until grafts have been rejected. Rats are dosed once, twice, or three times daily from Day 0 through Day 13. Each animal is anesthetized and an incision is made at the base of the recipient ear, cutting only the dorsal epidermis and dermis. The incision is spread open and down to the cartilage parallel to the head, and sufficiently wide to accommodate the appropriate tunneling for a rat or insertion tool for a mouse. A neonatal mouse or rat pup less than 60 hours old is anesthetized and cervically dislocated. The heart is removed from the chest, rinsed with saline, bisected longitudinally with a scalpel, and rinsed with sterile saline. The donor heart fragment is placed into the preformed tunnel with the insertion tool and air or residual fluid is gently expressed from the tunnel with light pressure. No suturing, adhesive bonding, bandaging, or treatment with antibiotics is required.

Implants are examined at 10- to 20-fold magnification with a stereoscopic dissecting microscope without anesthesia. Recipients whose grafts are not visibly beating may be anesthetized and evaluated for the presence of electrical activity using Grass E-2 platinum subdermal pin microelectodes placed either in the pinna or directly into the graft and a tachograph. Implants can be examined 1 to 4 times a day for 10, 20, 30, or more days. The ability of a test compound to ameliorate symptoms of transplant rejection can be compared with a control compound such as cyclosporine, tacrolimus, or orally-administered lefluonomide.

EXAMPLE 13

The analgesic activity of the compounds of the present invention is assessed by a test with rats. Rats weighing from 175 to 200 g are injected with carrageenan (2% in 0.9% sodium chloride aqueous solution, 100 $\mu$L injection volume) into the footpad of one hind limb. The rats are placed on a glass plate with illumination from a halogen lamp placed directly under the injected paw. The time (in seconds) from beginning illumination until the hindlimb was withdrawn from the glass was measured and scored as paw withdrawal latency (PWL). Drug substances were given by oral gavage injection 2.5 hours after carrageenan injection to the footpad. PWL was measured prior to carrageenan injection, just prior to drug injection, and 1, 2, (and sometimes 3) hours after drug injection.

Carrageenan (a polysaccharide extracted from seaweed) causes a sterile inflammation when injected under the skin.

Injection into the rat footpad causes little or no spontaneous pain-related behavior but induces hyperalgesia (pain-related behavioral responses of greater intensity than expected) to peripheral thermal or mechanical stimuli. This hyperalgesia is maximal 2 to 3 hours after injection. Treatment of rats with various analgesic drugs reduces hyperalgesia measured in this way and is a conventional test for detection of analgesic activity in rats. (Hargreaves K, Dubner R, Brown F, Flores C, Joris J. A new and sensitive method for measuring thermal nociception in cutaneous hyperalgesia. *Pain,* 1988;32:77–88 and Kayser V, Guilbaud G. Local and remote modifications of nociceptive sensitivity during carrageenan-induced inflammation in the rat. *Pain,* 1987;28:99–108). Untreated rats have a PWL of approximately 10 seconds. Carrageenan injection reduces PWL to approximately 3 seconds for at least 4 hours, indicating thermal hyperalgesia. Inhibition of the carrageenan thermal hyperalgesia response is determined by the difference between reduced PWL prior to drug and subsequent to drug treatment, and was expressed as percent inhibition of the response. Administration of MEK inhibitors dose-dependently reduced thermal hyperalgesia.

What is claimed is:

1. A compound of Formula

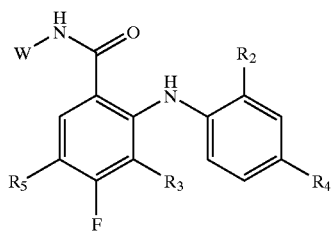

I wherein
W is

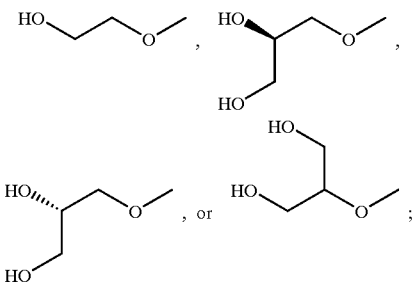

$R_2$ is hydrogen, methyl, fluorine, or chlorine;
$R_3$ is hydrogen or fluorine;
$R_4$ is —$CH_2S(CH_2)_m(CH_3)$, —C≡C$(CH_2)_q$NHCH$_3$, —C≡C—CH$_2$OCH$_3$, (Z)—CHCHCH$_2$OCH$_3$, —$(CH_2)_nCO_2R_6$, —$(CF_2)_pCF_3$, —$CH_2(CF_2)_qCF_3$, —$(CH_2)_mCF(CF_3)_2$, —CH$(CF_3)_2$, —CF$_2$CF$(CF_3)_2$, —C$(CF_3)_3$, —C≡C$(CH_2)_q$N$(CH_3)_2$, (Z)—CHCH—$(CH_2)_q$NHCH$_3$, or (Z)—CHCH—$(CH_2)_q$N$(CH_3)_2$, C(O)C$_{1-3}$ alkyl, or C(O)NHCH$_3$;
m is 0 to 1;
n is 0 to 2;
p is 1 to 5;
q is 1 to 2;
$R_5$ is hydrogen, fluorine, bromine, or chlorine;
$R_6$ is hydrogen, methyl or ethyl;
and pharmaceutically acceptable salts thereof.

2. The compound of claim 1 wherein W is

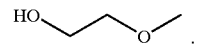.

3. The compound of claim 1 wherein W is

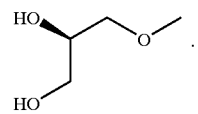.

4. The compound of claim 1 wherein W is

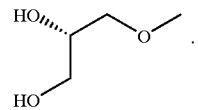.

5. The compound of claim 1 wherein W is

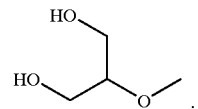.

6. The compound of claim 1 wherein $R_2$ is hydrogen, fluorine, or chlorine.
7. The compound of claim 1 wherein $R_3$ is fluorine.
8. The compound of claim 1 wherein $R_4$ is —(CH$_2$)$_n$CO$_2$R$_6$.
9. The compound of claim 1 wherein $R_4$ is —C≡C—CH$_2$OCH$_3$.
10. The compound of claim 1 wherein $R_4$ is C(O)CH$_3$.
11. The compound of claim 1 wherein $R_5$ is hydrogen.
12. A compound of Formula

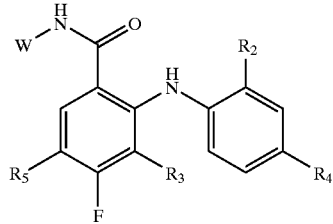

wherein
W is

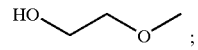;

$R_2$ is hydrogen, fluorine, or chlorine;
$R_3$ is fluorine;
$R_4$ is —$CH_2S(CH_2)_m(CH_3)$, —C≡C—CH$_2$OCH$_3$, (Z)—CHCHCH$_2$OCH$_3$, —$(CH_2)_nCO_2R_6$, —$(CF_2)_pCF_3$, —$CH_2(CF_2)_qCF_3$, —$(CH_2)_mCF(CF_3)_2$, —CH$(CF_3)_2$, —CF$_2$CF$(CF_3)_2$, —C$(CF_3)_3$, —(Z)—CHCH—$(CH_2)_q$NHCH$_3$, or (Z)—CHCH—$(CH_2)_q$N$(CH_3)_2$, or C(O)CH$_3$;
n is 0;
$R_5$ is hydrogen;
$R_6$ is hydrogen or methyl;
and pharmaceutically acceptable salts thereof.

13. A compound of Formula

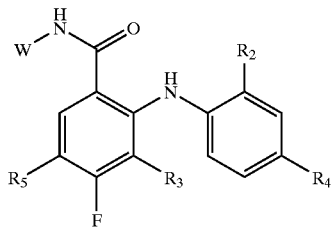

wherein
W is

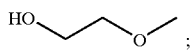

R₂ is hydrogen, fluorine, or chlorine;
R₃ is fluorine;
R₄ is —C≡C—CH₂OCH₃, —(CH₂)ₙCO₂R₆ or C(O)CH₃;
n is 0;
R₅ is hydrogen;
R₆ is hydrogen or methyl;
and pharmaceutically acceptable salts thereof.

14. A pharmaceutical composition comprising a compound of claim 1 and a pharmaceutically acceptable carrier.

15. A method of treating a proliferative disease in a patient in need thereof comprising administering a therapeutically effective amount of a compound of claim 1.

16. A method of claim 15 wherein the proliferative disease is selected from the group consisting of cancer, restenosis, psoriasis, and atherosclerosis.

17. A method of treating psoriasis in a patient in need thereof comprising administering a therapeutically effective amount of a compound of claim 1.

18. A method of treating cancer in a patient in need thereof comprising administering a therapeutically effective amount of a compound of claim 1.

19. A method of claim 18 wherein the cancer is MEK-related.

20. A method of claim 18 wherein the cancer is brain, breast, lung, ovarian, pancreatic, prostate, renal, or colorectal cancer.

21. A method of treating osteoarthritis in a patient in need thereof comprising administering a therapeutically effective amount of a compound of claim 1.

22. A method of treating rheumatoid arthritis in a patient in need thereof comprising administering a therapeutically effective amount of a compound of claim 1.

23. A method of treating heart failure in a patient in need thereof comprising administering a therapeutically effective amount of a compound of claim 1.

24. A method of treating chronic pain in a patient in need thereof comprising administering a therapeutically effective amount of a compound of claim 1.

25. The method of claim 24, wherein the chronic pain is selected from the group consisting of neuropathic pain, idiopathic pain, and pain associated with chronic alcoholism, vitamin deficiency, uremia, and hypothyroidism.

26. The method of claim 24, wherein the chronic pain is associated with inflammation.

27. The method of claim 24, wherein the chronic pain is associated with arthritis.

28. The method of claim 24, wherein the chronic pain is associated with post-operative pain.

29. A method of treating neuropathic pain in a patient in need thereof comprising administering a therapeutically effective amount of a compound of claim 1.

30. The method of claim 29, wherein the neuropathic pain is associated with a condition selected from the group consisting of inflammation, postoperative pain, phantom limb pain, burn pain, gout, trigeminal neuralgia, acute herpetic and postherpetic pain, causalgia, diabetic neuropathy, plexus avulsion, neuroma, vasculitis, viral infection, crush injury, constriction injury, tissue injury, limb amputation, arthritis pain, and nerve injury between the peripheral nervous system and the central nervous system.

31. A method for treating cancer in a patient in need thereof comprising administering a therapeutically effective amount of a compound of claim 1 in combination with radiation therapy.

32. A method for treating cancer in a patient in need thereof comprising administering a therapeutically effective amount of a compound of claim 1 in combination with at least one chemotherapeutic agent.

33. A method of claim 29 wherein the chemotherapeutic agent is a mitotic inhibitor.

34. A method of claim 30 wherein the mitotic inhibitor is selected from the group consisting of paclitaxel, docetaxel, vincristine, vinblastine, vinorelbine, and vinflunine.

35. A compound which is selected from the group consisting of
   Methyl 4-[[2,3-difluoro-6-[[(2-hydroxyethoxy)amino]carbonyl]-phenyl]amino]benzoate;
   4-[[2,3-Difluoro-6-[[(2-hydroxyethoxy)amino]carbonyl]phenyl]-amino]benzoic acid;
   3,4-Difluoro-2-[[2-fluoro-4-(3-methoxy-1-propynyl)phenyl]-amino]-N-(2-hydroxyethoxy)benzamide;
   Methyl 4-(2,3-difluoro-6-{[(2-hydroxyethoxy)amino]carbonyl}anilino)-3-fluorobenzoate;
   4-(2,3-Difluoro-6-{[(2-hydroxyethoxy)amino]carbonyl}anilino)-3-fluorobenzoic acid;
   2-(4-Acetyl-2-chloro-phenylamino)-3,4-difluoro-N-(2-hydroxy-ethoxy)-benzamide; and
   2-{2-fluoro-4-[(methylamino)carbonyl]anilino}-3,4-difluoro-N-(2-hydroxyethoxy)benzamide.

* * * * *